United States Patent [19]
Townsend et al.

[11] Patent Number: 6,066,102
[45] Date of Patent: May 23, 2000

[54] OPTICAL BIOPSY FORCEPS SYSTEM AND METHOD OF DIAGNOSING TISSUE

[75] Inventors: Greg L. Townsend, Plymouth; Brian T. McMahon, Minnetonka; Chester E. Sievert, Jr., Mahtomedi; Scott R. Wilson, Maple Grove; James L. Pokorney, Northfield, all of Minn.; John P. Farris, Plymouth, N.H.; David E. Porter, Center Sandwich, N.H.; Mark H. Feddern, Chocorua, N.H.

[73] Assignee: SpectraScience, Inc., Plymouth, Minn.

[21] Appl. No.: 09/037,240

[22] Filed: Mar. 9, 1998

[51] Int. Cl.⁷ .................................................. A61B 10/00
[52] U.S. Cl. ........................... 600/564; 600/104; 600/153; 606/170; 606/174
[58] Field of Search ..................................... 600/104, 153, 600/154, 156, 562, 564, 566, 567, 101; 606/51, 52, 167, 170, 174, 205

[56] References Cited

U.S. PATENT DOCUMENTS

| | | | |
|---|---|---|---|
| 3,074,408 | 1/1963 | Chester | 128/328 |
| 3,924,608 | 12/1975 | Mitsui | 128/2 B |
| 3,961,621 | 6/1976 | Northeved | 128/2 B |
| 4,027,510 | 6/1977 | Hiltebrandt | 72/37 |
| 4,421,106 | 12/1983 | Uehara | 128/4 |
| 4,557,255 | 12/1985 | Goodman | 128/7 |
| 4,573,450 | 3/1986 | Arakawa | 128/6 |
| 4,620,547 | 11/1986 | Boebel | 128/754 |
| 4,646,751 | 3/1987 | Maslanka | 128/751 |
| 4,656,999 | 4/1987 | Storz | 128/4 |
| 4,887,612 | 12/1989 | Esser et al. | 128/751 |
| 5,228,451 | 7/1993 | Bales et al. | 128/751 |
| 5,280,788 | 1/1994 | Janes et al. | 128/665 |
| 5,291,010 | 3/1994 | Tsuji | 250/208.1 |
| 5,318,023 | 6/1994 | Vari et al. | 128/633 |
| 5,354,291 | 10/1994 | Bales et al. | 604/35 |
| 5,373,854 | 12/1994 | Kolozsi | 128/749 |
| 5,439,000 | 8/1995 | Gunderson et al. | 128/664 |
| 5,467,767 | 11/1995 | Alfano et al. | 128/665 |
| 5,471,992 | 12/1995 | Banik et al. | 128/751 |
| 5,482,054 | 1/1996 | Slater et al. | 128/751 |
| 5,536,248 | 7/1996 | Weaver et al. | 604/54 |
| 5,558,100 | 9/1996 | Cox | 128/751 |
| 5,562,100 | 10/1996 | Kittrell et al. | 128/665 |
| 5,562,102 | 10/1996 | Taylor | 128/751 |
| 5,571,129 | 11/1996 | Porter | 606/170 |
| 5,601,087 | 2/1997 | Gunderson et al. | 128/664 |
| 5,667,473 | 9/1997 | Finn et al. | 600/104 |
| 5,762,613 | 6/1998 | Sutton et al. | 600/564 |
| 5,843,000 | 12/1998 | Nishioka et al. | 600/567 |
| 5,848,978 | 12/1998 | Cecchi | 600/567 |
| 5,857,961 | 1/1999 | Vanden Hoek et al. | 600/104 |
| 5,908,381 | 6/1999 | Aznoian et al. | 600/104 |

FOREIGN PATENT DOCUMENTS

| | | | |
|---|---|---|---|
| 316816 | 11/1988 | European Pat. Off. | 600/182 |
| 0321132A2 | 6/1989 | European Pat. Off. | A61M 25/00 |
| 0512965 | 11/1992 | European Pat. Off. | A61B 5/00 |
| 0593929 | 4/1994 | European Pat. Off. | A61B 17/00 |
| 3920706A1 | 1/1991 | Germany | A61B 17/28 |
| 19533856 | 3/1997 | Germany | A61B 19/00 |
| 83/03189 | 9/1983 | WIPO | |
| 94/12095 | 6/1994 | WIPO | |
| 97/41776 | 11/1997 | WIPO | A61B 10/00 |
| 97/41777 | 11/1997 | WIPO | A61B 10/00 |

*Primary Examiner*—Cary O'Connor
*Assistant Examiner*—Charles Marmor, II
*Attorney, Agent, or Firm*—Schwegman, Lundberg, Woessner & Kluth, P.A.

[57] ABSTRACT

A biopsy forceps device is provided for obtaining tissue samples at a site within the body, while maintaining access to the site through an access lumen of the biopsy forceps. The device includes an elongate tubular body for introduction into the body and navigation to an area of interest. An inner tubular member having a lumen, or a plurality of lumens, extends through or adjacent the outer tubular member, from the proximal end to the distal end, where cutting jaws are provided. The cutting jaws are rotatably mounted at the distal end of the device and are controlled by movement of the inner tubular member. The inner tubular member is coupled with a handle portion allowing control of the cutting jaws at the proximal end. Access to the lumen of the inner tubular member is gained at the proximal end, where a luer fitting is provided. The lumen of the inner tubular member has a removable optical fiber disposed therethrough and allows for a variety of medical instruments to be inserted so that the instruments can be used coaxially in the same location as where the biopsy sample is taken.

49 Claims, 13 Drawing Sheets

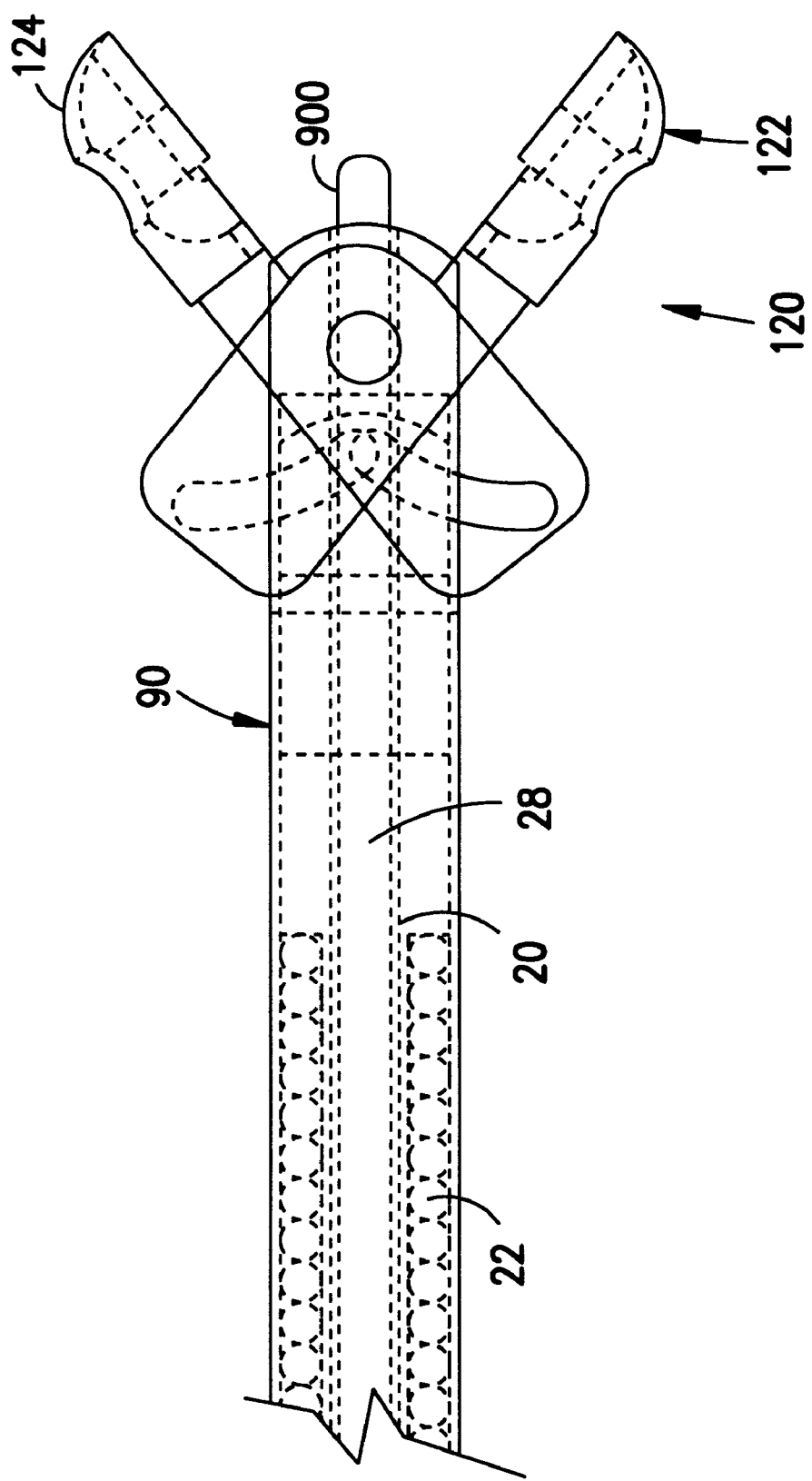

OPTICAL BIOPSY FORCEPS SYSTEM AND METHOD OF DIAGNOSING TISSUE

CROSS REFERENCE TO RELATED APPLICATIONS

This application is related to the following co-pending, commonly assigned U.S. patent applications: application Ser. No. 09/037,722, entitled "OPTICAL BIOPSY SYSTEM AND METHODS FOR TISSUE DIAGNOSIS," filed on even date herewith, and application Ser. No. 08/644,080, entitled "OPTICAL BIOPSY FORCEPS," each of which is assigned to the assignee of the present invention, and the entire disclosure of each being incorporated herein by reference.

FIELD OF THE INVENTION

The present invention relates generally to medical diagnosis and treatment. More particularly, it pertains to a reusable and disposable biopsy forceps device having an optical fiber for optical biopsy and histopathological analysis of tissue.

BACKGROUND OF THE INVENTION

Numerous types of biopsy forceps have been developed for in vivo medical diagnosis and treatment of various conditions. Such devices are designed for sampling tissue within the body, for example in endoscopic, laparoscopic and vascular procedures to retrieve biopsy samples for analysis and identification of tissue types. These biopsy forceps devices generally include small cutting jaws at the distal end, operated remotely from the proximal end after the distal end of the device has been positioned or navigated to the site of interest.

One difficulty in using prior art biopsy forceps devices is in knowing for certain the exact positioning of the distal tip, in relation to the suspected disease area, especially when the area of interest is very small. Another difficulty of prior art biopsy forceps in combination with other endoscopic accessories is the exact positioning of both instruments. Various types of optical catheters or probes have been developed for use in locating or identifying sites within the body. A method of diagnosing in vivo using an optical guidewire is disclosed in U.S. Pat. No. 5,439,000, assigned to SpectraScience, Inc. An apparatus and method for identifying and obtaining a biopsy sample is disclosed in pending U.S. application Ser. Nos. 08/643,912 and 08/644,080 licensed and assigned, respectively, to SpectraScience, Inc. The applications are entitled "Optical Biopsy Forceps and Method of Diagnosing Tissue" and "Optical Biopsy Forceps," respectively.

One type of prior art system for internal biopsy uses an optical catheter to locate the site, followed by replacement of the optical catheter with a biopsy forceps for taking a tissue sample. However, this can result in errors and uncertainties in the final placement of the biopsy jaws with respect to a previously identified small structure or targeted area since the exact site identified by the optical catheter is not treated with the biopsy forceps or other instruments to treat the site.

Other prior art systems have been proposed which use optical viewing or imaging and a cutting device in the same device, to visually locate and then biopsy a suspected area. However, such devices have been hampered by their thickness which is needed to accommodate the imaging system and the cutting actuation system, and which precludes their use in very small areas. Another shortcoming of such prior art systems is the offset or 'parallax' between the viewing axis or the imaging system and the cutting position of the biopsy jaws, such that the biopsy sample actually is taken from a zone slightly displaced from the zone being viewed by the optics. This can result in a loss of accuracy in the case of very small structures of interest.

Another difficulty in conventional devices is accessing the area from which the biopsy sample is to be taken. Often the area to be sampled requires treatment before the sample is taken. An optical catheter is used to locate the biopsy site, followed by replacement of the optical catheter with a medical instrument for treating the area. The instrument is removed, and biopsy forceps is inserted for taking a biopsy sample. However, this can result in errors and uncertainties in the final placement of the biopsy jaws with respect to a previously identified small structure or biopsy area.

Other biopsy devices allow for a biopsy sample to be pierced with a spike before the biopsy sample is taken. However, these devices are limited to the fixed instrument disposed within the forceps. If additional instruments and treatment is necessary for the biopsy area, the biopsy device must be removed from the body, and a different device inserted into the body. Removing the device to insert another poses additional problems in that the exact biopsy location will not be treated.

Accordingly, a better way to treat biopsy areas is needed. What is further needed is a device to accommodate multiple methods of treatment for an exact biopsy area. What is also needed is a better way to obtain a biopsy sample.

SUMMARY OF THE INVENTION

To overcome these and other problems, an integrated biopsy forceps device is provided, which is very thin, with an access lumen enabling the device to be used in very small areas of interest, and which allows for accurate alignment with repetitive withdrawal or introductions of various adjunctive medical instruments to treat the biopsy sampling area. A system is also provided where an integrated biopsy forceps device is coupled with an electro-optical diagnostic apparatus for optical biopsy to perform histopathological analysis of tissue.

The present invention, in one embodiment, provides a biopsy forceps which is adapted for tissue treatment and identification through the access lumen and by biopsy sampling. The forceps device includes an elongated catheter body for introduction into the body and navigation to an area of interest. The distal end of the forceps device has a pair of cutting jaws, and a lumen extends through the forceps device aligning with the closed cutting position of the cutting jaws. The proximal end has a handle portion for manipulating the forceps device and actuating the jaws.

In accordance with one aspect of the invention, there is provided a method of treating tissue at a site within a body. The method comprises introducing into the body a biopsy forceps which includes a flexible catheter body with an access lumen extending therethrough with the distal end of the lumen aligned with a biopsy sampling area adjacent the distal tip of the catheter body. Instruments such as an optical fiber, are inserted into the device and through the lumen to treat the sampling area as appropriate. The biopsy forceps additionally include cutting jaws mounted at the distal end of the catheter body for selective opening and closing in a biopsy cutting movement in the biopsy sampling area, and an actuator mechanism operatively connected to the jaws for selectively controlling the opening and closing of the cutting jaws. Then, tissue in the biopsy sampling area adjacent the distal end of the forceps is treated with the instruments inserted through the forceps or identified by the optical fiber coupled with the electro-optical diagnostic apparatus. Alternatively, the area is flushed with medicine or saline with or without the optical fiber inserted in the lumen. Then, a biopsy sample is cut from the location of the optical tissue analysis zone by actuating the actuator mechanism, and the biopsy sample is withdrawn from the body.

In one embodiment, the cutting jaws are mounted for pivoting about stationary pivot pins for cutting tissue placed there between, and coupled to and controlled by an inner tubular member forming the lumen that extends through the catheter body to the handle portion at the proximal end of the device. The inner tubular member extends through the handle and couples with an access portion on the handle portion. Instruments, medicine, or fluids are inserted into the access portion and through the lumen to treat, flush, or clean the biopsy sampling area. The inner tubular member is positioned coaxially with the jaws, so that the biopsy sample is taken exactly at the spot where treatment with instruments or fluids took place. In an alternative configuration, a second lumen is provided adjacent the lumen within the inner tubular member to provide additional access proximate the biopsy sampling area.

In another embodiment, the cutting jaws are mounted for pivoting about stationary pivot pins for cutting tissue placed therebetween, and controlled by control wires extending through the catheter body to the control handle and/or an inner member. Alternatively, the cutting jaws are rotatably coupled with a distal housing and are controlled by links. The links, in another embodiment, are operatively coupled with the actuator housing and the cutting jaws. The inner member has a lumen therein and extends through the device, from its proximal end for coupling with an access port. An optical fiber is disposed within the lumen of the inner member. The control wires are disposed in grooves formed in the inner member and the wires and the inner member are coupled with a handle for actuating the cutting jaws.

In yet another embodiment, the cutting jaws are mounted for pivoting about stationary pivot pins and are for cutting tissue placed between the cutting jaws, and coupled to and controlled by an inner tubular member that extends through the catheter body to the handle portion at the proximal end of the device. The inner tubular member has a plurality of lumens therein with an optical fiber disposed in at least one of the lumens, and extends through the handle and couples with an access portion on the handle portion. Instruments, medicine, or fluids are inserted into the access portion and through the lumen to treat the biopsy sampling area. The inner tubular member is positioned coaxially with the jaws, so that the biopsy sample is taken exactly at the spot where treatment with instruments or fluids took place.

According to one aspect of the invention, the biopsy forceps is reusable. When the optical fiber needs to be replaced, the entire biopsy forceps does not need to be discarded. Instead, a new optical fiber is inserted through the central access lumen when the use of the previous optical fiber is exhausted. Removing the optical fiber from the biopsy forceps also allows for the forceps to be cleaned and sterilized more extensively using more thorough and strenuous processes.

According to another aspect of the invention, the biopsy forceps is disposable. Using disposable biopsy forceps helps to reduce the chance of contamination between patients where a biopsy forceps is disposed after use on one patient, which is ideal for patients with highly contagious and dangerous diseases or patients highly susceptible to infection.

One important use of the invention is in connection with endoscopic treatment and diagnosis procedures, for example in gastrointestinal endoscopy or bronchoscopy. The present invention is also useful in many other endoscopic fields including, but not limited to: urology, cardiovascular, neurology, orthopedics, general surgery, laparoscopy, obstetrics/gynecology, etc. It can also be used in minimally invasive laparoscopic procedures for additional diagnostic information, and/or guidance of a therapeutic modality (e.g., laser or cutting/coagulation devices, such as a bipolar or monopolar electrocautery RF device).

These and other features and advantages of the invention will become apparent from the following description of the preferred embodiments of the invention.

BRIEF DESCRIPTION OF THE DRAWINGS

FIG. 3 is a first side elevational view illustrating biopsy forceps constructed in accordance with one embodiment of the present invention.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims.

Figure 1:
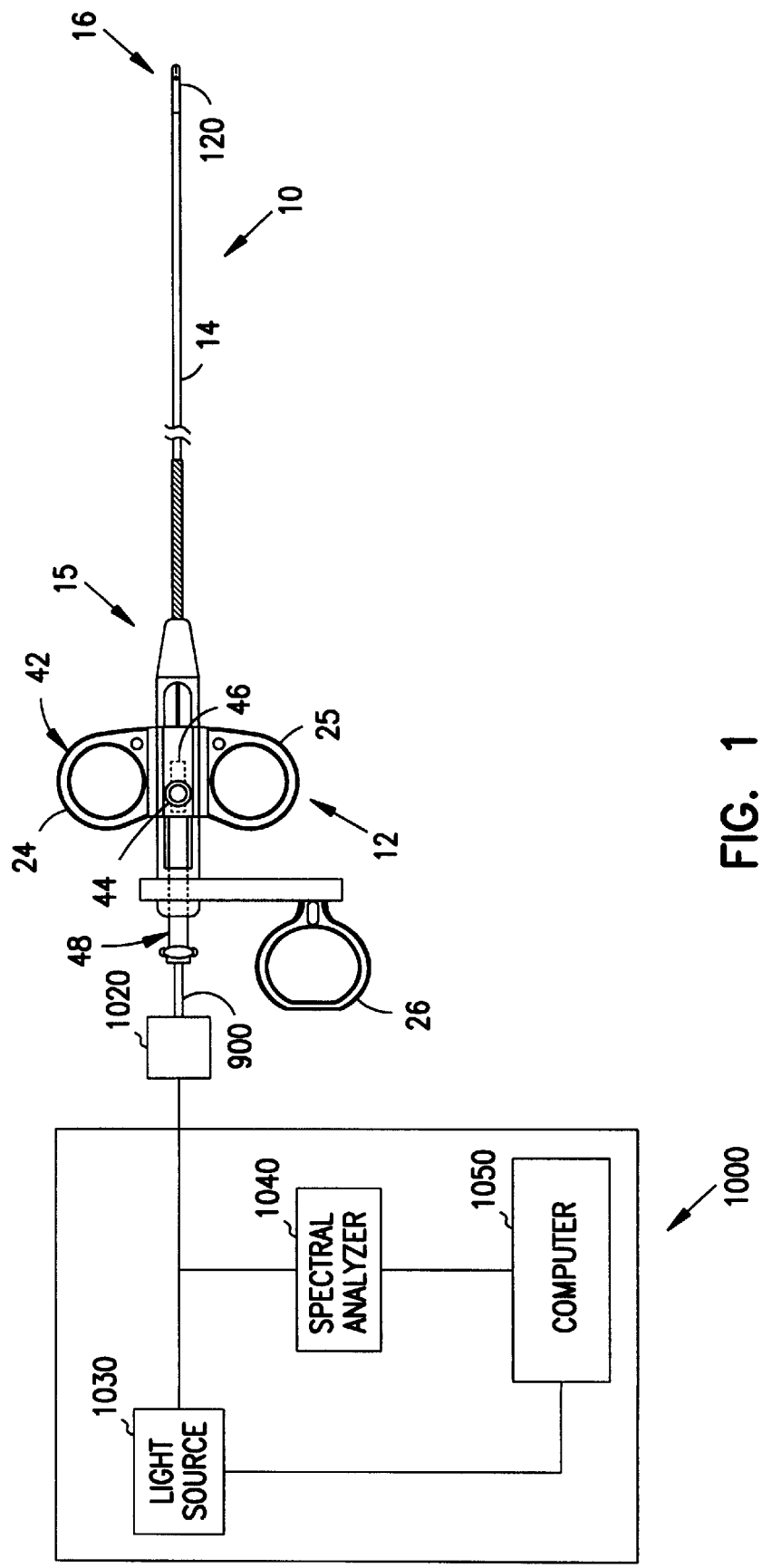
FIG. 1 is a first side elevational view of a biopsy forceps connected to a diagnostic apparatus shown in schematic diagram constructed in accordance with one embodiment of the present invention.

FIG. 1 illustrates a system including a biopsy forceps 10 and a diagnostic apparatus 1000, such as a spectrophotometer. In one embodiment, the electro-optical diagnostic apparatus 1000 comprises a light source 1030, a spectral analyzer 1040, and a computer 1050. Forceps 10 includes an optical fiber 900 disposed therethrough, as is explained in greater detail below. The optical fiber 900 is coupled with the fiber coupler 1020 and the light source 1030 of the diagnostic apparatus 1000.

During use, the light source 1030 provides a source of optical radiation, where operation of the light source 1030 is, in one embodiment, controlled by the computer 1050. Operation of the light source 1030 transmits radiation into the fiber coupler 1020. The radiation emanates from the optical fiber 900 upon a tissue location (not shown). The radiation returning from the tissue by reflection or fluorescence is received by the optical fiber 900 and the fiber coupler 1020 which then transmits the returning radiation to the spectral analyzer 1040. In another embodiment, the computer 1050 further analyzes the information from the spectral analyzer 1040 and outputs the information to a display (not shown). The system is not limited to the diagnostic technique described above. Rather, the system according to the present invention is designed for use in methods utilizing any optically based diagnostic techniques, including laser induced fluorescence, time-resolved fluorescence, Raman spectroscopy, optical coherence tomography, etc. Alternative techniques of diagnosing tissue from the data received from the optical fiber will be known to those skilled in the art and will not be described further herein.

Figure 2:
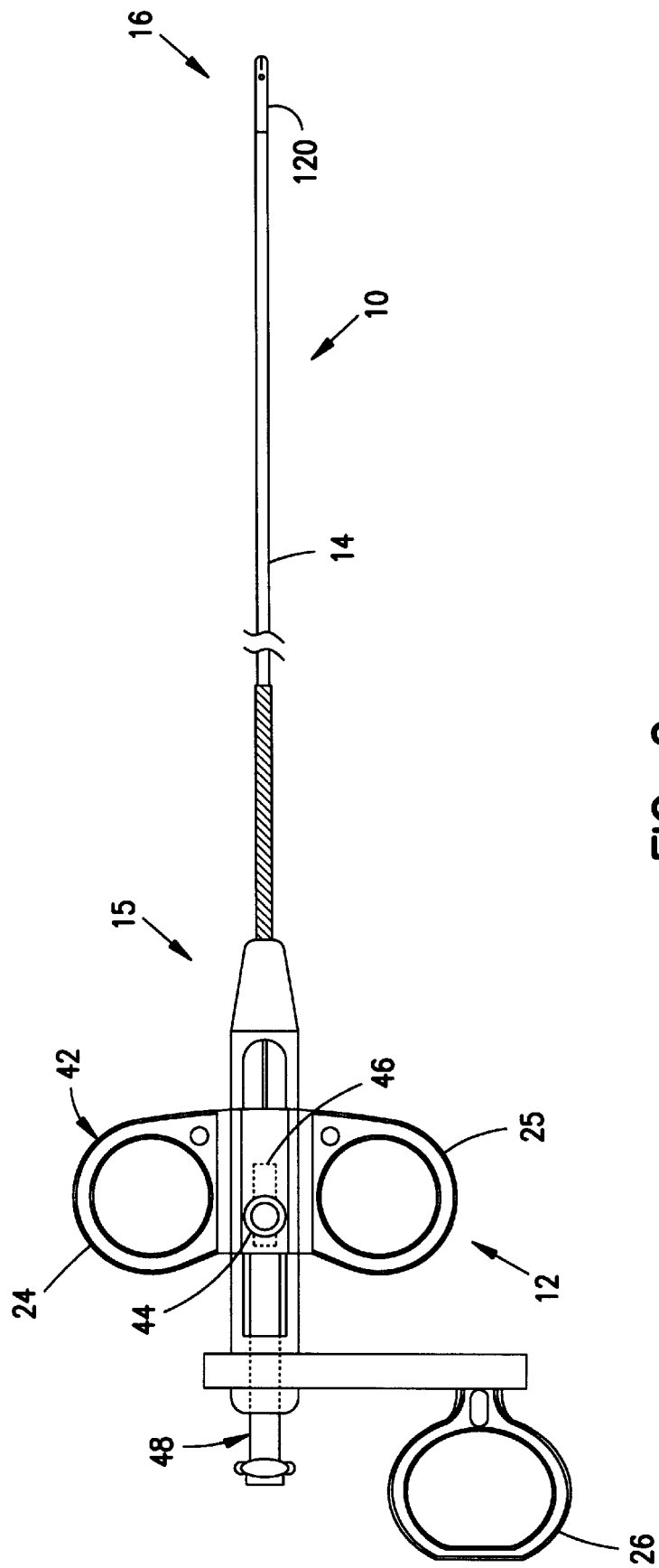
FIG. 2 is a first side elevational view illustrating biopsy forceps constructed in accordance with one embodiment of the present invention.

The biopsy forceps 10 is shown in greater detail in FIG. 2. The biopsy forceps 10 is adapted for use internally of the body, for example in connection with endoscopic, laparoscopic or vascular procedures. Forceps 10 includes a control handle portion 12 at a proximal end 15, a middle portion 14 which extends over the main length of the device, and a distal end 16 which includes opposed forceps cutting jaws 120, as is explained in greater detail below.

The main body or length of the forceps 10 consists of coaxial inner and outer tubular members 20, 22, as shown in more detail in FIG. 3. The outer tubular member 22 is small enough such that it can be inserted within a working channel of an endoscope. In one embodiment, the inner tubular member 20 is a stainless steel tube, and the outer tubular member 22 or catheter body is a coil. In another embodiment, the inner tubular member 20 comprises a coiled stainless steel tube. For either the inner tubular member 20 or the outer tubular member 22 having the coiled stainless steel configuration, the coil is a finely wound spiral coil of stainless steel as is generally known and used in catheters and guidewires. Alternatively, the outer tubular member 22 or the inner tubular member 20 could be made using a plastic tube, or a plastic/metal composite structure, in place of the coil.

The inner tubular member 20 is positioned within the outer tubular member 22 and these components are dimensioned with respect to each other so that inner tubular member 20 moves freely within the outer tubular member 22 to actuate the jaws, as is explained in more detail below. The inner tubular member 20 has a central access lumen 28 extending through the inner tubular member 20 from the proximal end 15 to the distal end 16. The access lumen 28 is sized to receive the optical fiber 900 therethrough. The optical fiber 900, in one embodiment, is removably disposed within the access lumen 28. The access lumen 28 is sized larger than the optical fiber 900, in one embodiment, such that a fluid (e.g. saline) can be flushed through the forceps 10 to clean the lumen 28, the area of interest or to clean the distal portion of the optical fiber 900. In another embodiment, a variety of medical instruments can be inserted through the lumen 28 when the optical fiber 900 is removed, as shown in FIGS. 16a–16g, and as will be discussed further below. The inner tubular member 20 is coupled with an actuator housing 60.

Figure 4A:
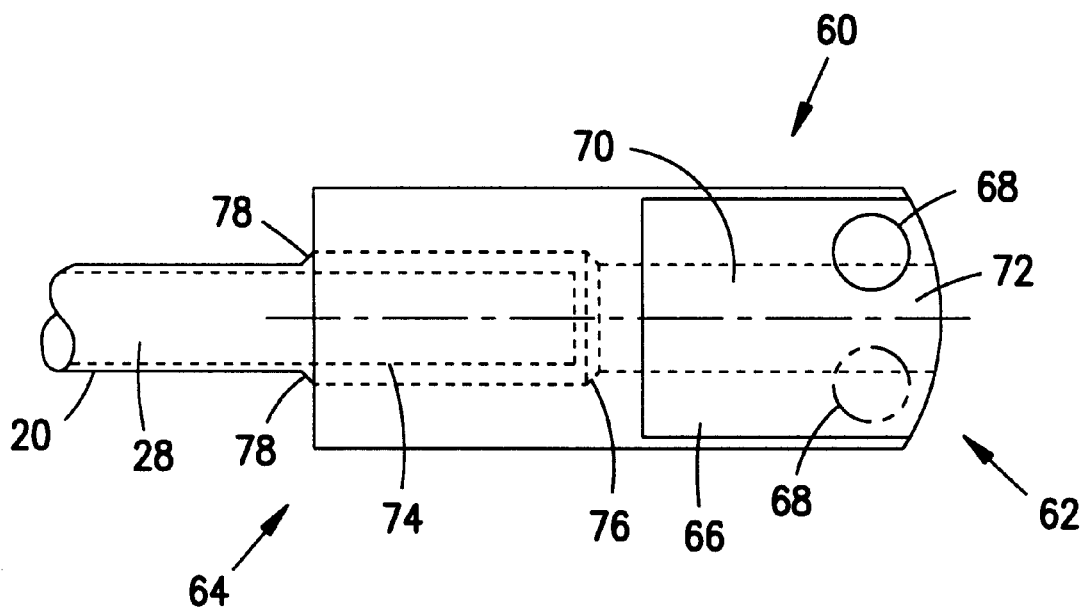
FIG. 4a is a first side elevational view illustrating an actuator housing for use with biopsy forceps constructed in accordance with one embodiment of the present invention.
Figure 4B:
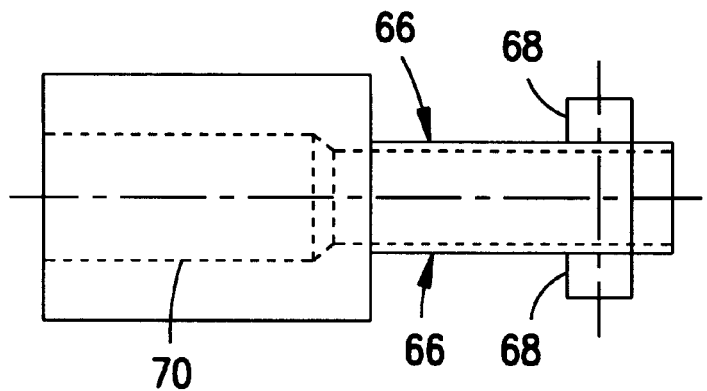
FIG. 4b is a second side elevational view illustrating the actuator housing for use with biopsy forceps constructed in accordance with one embodiment of the present invention.

The actuator housing 60, shown in more detail in FIGS. 4a and 4b is, in one embodiment, fabricated from stainless steel material. Alternatively, the actuator housing 60 can be formed from other substantially rigid materials. The actuator housing 60 extends from a first end 62 to a second end 64, and generally comprises an elongate cylinder. In addition, the actuator housing 60 has flats 66 formed proximate the first end 62. Disposed on the flats 66 are cam pins 68 having a generally circular cross-section, as shown. In one embodiment, the cam pins 68 are integral with the flats 66 of the actuator housing 60. To form the cam pins 68 integrally with the flats 66, the actuator housing 60 can be machined or molded from a single piece of material. Alternatively, the cam pins 68 can be integrally formed with the flats 66 by attaching the projections to the flats 66 using, for example, adhesive or welding processes. The cam pins 68 are for coupling with the jaws, as will be further explained below.

The actuator housing 60 has a bore 70 extending from the first end 62 to the second end 64, where the bore has a first portion 72 and a second portion 74. The first and second portions 72, 74 form a shoulder 76 in between. The first portion 72 has a smaller diameter than the inner tubular member 20, yet large enough to allow the optical fiber 900 to pass through the first portion 72. In one embodiment, the first portion 72 is large enough to allow other medical devices to pass through, such as the devices shown in FIGS. 16a–16g. The inner tubular member 20 is inserted within the second portion 74 of the actuator housing 60 until, in one embodiment, inner tubular member 20 contacts the shoulder 76 of the actuator housing 60. In another configuration, the inner tubular member 20 can be placed proximate to shoulder 76. The access lumen 28 of the inner tubular member 20 is substantially aligned with the bore 70 of the actuator housing 60, thereby facilitating insertion of the optical fiber 900 or the medical devices through the access lumen 28 and through the bore 70. The inner tubular member 20 is coupled with the actuator housing 60, where in one embodiment, the inner tubular member 20 is secured to the actuator housing 60 with a weld 78. Alternatively, the inner tubular member 20 can be joined with the actuator housing 60 by solder, brazing, or adhesive techniques as is known by those skilled in the art.

Figure 5A:
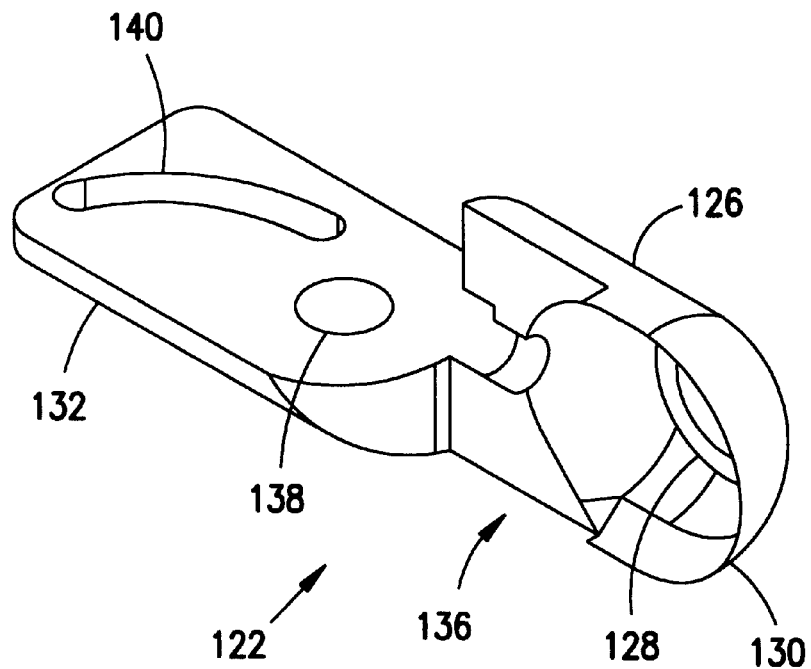
FIG. 5a is a perspective view illustrating a cutting jaw for use with biopsy forceps constructed in accordance with one embodiment of the present invention.
Figure 5B:
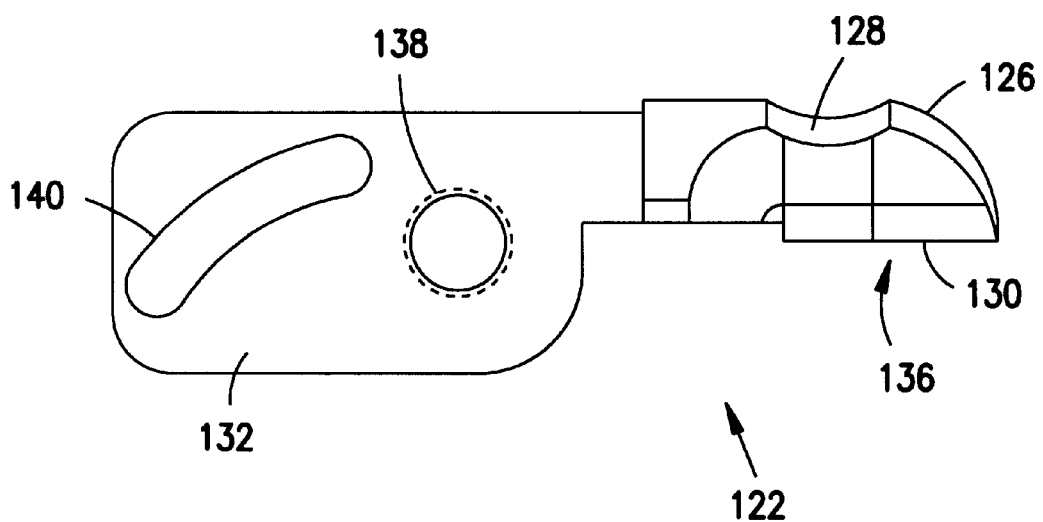
FIG. 5b is a first side elevational view illustrating a cutting jaw for use with biopsy forceps constructed in accordance with one embodiment of the present invention.

FIGS. 3, 5a and 5b show the cutting jaws 120 in more detail. The cutting jaws 120 are comprised of a first jaw 122 and a second jaw 124 which, in one embodiment, are mirror images of each other. Since the first jaw 122 and the second jaw 124 are similar, only the first jaw 122 will be discussed. The jaw 122 has an actuation portion 132 and a cutting portion 136. Within the cutting portion 136, the jaw 122 has a hemispherical cup 126 with sharpened edges 130 for taking biopsy samples. The cup 126 of jaw 122 has, in one embodiment, a hole 128 disposed therein. The hole 128 advantageously facilitates cutting the biopsy sample at the site within the body, and also facilitates the removal of the biopsy specimens captured by each cup 126.

Referring to the actuation portion 132, the jaw 122 has a cut out 138 for forming a pivot point for the jaw 122. The cut out 138 is generally circular in shape and sized to receive a projection of a distal housing, as will be further discussed below. The actuation portion 132 also includes a cam slot 140, which in one embodiment is arcuately shaped. The cam slot 140 couples with the cam pin 68 of the actuator housing 60. The cam slot 140 is sized to receive the cam pin 68 therein, and allows for radial movement of the jaw 122 about the pivot point as the cam pin 68 of the actuator housing 60 is moved along the axis of the biopsy forceps 10. The movement of the jaw 122 about the pivot point allows for radial movement of the cutting jaws 120, without axial movement of the cutting jaws 120. This provides a further benefit since the jaws more accurately cut the biopsy sample at the exact position identified using the optical fiber 900.

Figure 6:
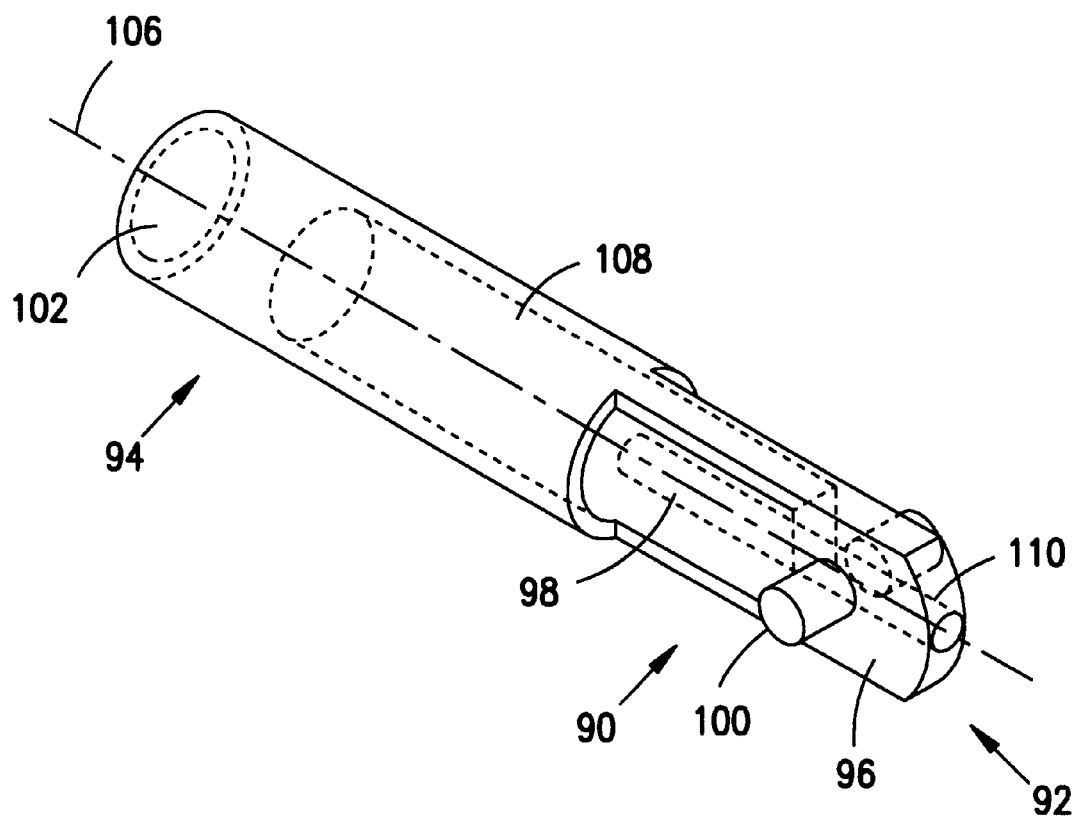
FIG. 6 is a perspective view illustrating a distal housing for use with biopsy forceps constructed in accordance with one embodiment of the present invention.

Biopsy forceps 10 also includes a distal housing 90, as shown in more detail in FIG. 6. The distal housing 90 is a generally elongate cylinder having a radial axis 106 and extending from a first end 92 to a second end 94. The housing 90 is fabricated from, in one embodiment, stainless steel material. Disposed proximate the first end 92 are flats 96. In one embodiment, the flats 96 each form a surface which is parallel to each other. The flats 96 each have a pivot pin 100 disposed thereon. The pivot pin 100 couples with the cut out 138 in each of the cutting jaws 120, and allows the cutting jaws 120 to rotate about the pivot pin 100. The flats 96 have a cut out 98 extending through the housing 90. In one embodiment, the cut out 98 is generally square shaped and is disposed perpendicular to the radial axis 106 of the housing 90, as shown in FIG. 6. The cut out 98 is sized to allow the actuator housing 60 to travel along the radial axis 106 of the housing 90 sufficient to actuate the cutting jaws 120 without interference from the distal housing 90.

Extending through the housing 90 is a bore 102. The bore 102 is aligned with the radial axis 106 of the housing 90 and extends from the first end 92 to the second end 94. The bore 102 has its largest diameter proximate the second end 94, and tapers to a second bore portion 108. The housing 90 has a third bore portion 110 proximate the first end 92 of the housing 90. The bore 102 is sized to receive the outer tubular member 22 therein. The outer tubular member 22 is secured to the housing 90 by welding, brazing, soldering, adhesives, or other equivalents known to those skilled in the art. The second bore portion 108 is sized to receive the actuator housing 60 therethrough, and to allow the actuator housing 60 to travel axially to actuate the jaws 120. The third bore portion 110 is sized to freely receive the optical fiber 900 or medical devices such as those shown in FIGS. 16a–16g, such that the fiber 900 or the devices can be used through the cutting jaws 120.

Referring again to FIG. 1, the biopsy forceps 10 includes the handle portion 12 for facilitating actuation of the inner tubular member 20. The handle portion 12 includes a handle 42 and a translation member 46, and loops 24, 25, 26. Loops 24, 25, 26 are provided in the handle portion 12 to form finger holes useful in grasping and manipulating the forceps 10. The handle 42 is fastened to the translation member with a fastener 44. The inner tubular member 20 is fastened to the translation member by welding, brazing, soldering, adhesives, or other mechanical fasteners such that movement of the handle 42 results in movement of the inner tubular member 20. In addition, a luer fitting 48 is threaded into the translation member 46. The translation member 46 has a bore (not shown) therethrough, which provides a conduit between the luer fitting 48 and the inner tubular member 20. The luer fitting 48 in combination with the bore of the translation member 46 provide access to the lumen 28 and allows for ease of cleaning and reusability of the biopsy forceps 10. The handle portion 12 can include any type of actuating mechanism capable of imparting bidirectional axial movement to the inner tubular member 20 of biopsy forceps 10.

Referring to FIGS. 1 and 2, in operation, the handle 42 is retracted toward the back of handle portion 12 to close the jaws. Retraction of the handle 42 causes movement of the inner tubular member 20 and the actuator housing 60 toward the handle portion 12, and closes the cutting jaws 120. In this configuration, the distal end 16 of the forceps 10 is of the same narrow diameter as the main body of a forceps catheter, and the closed jaws have a smooth, rounded shape to facilitate introduction and navigation in the vascular, endoscopic or laparoscopic systems. In addition, the cutting jaws are coaxially positioned with respect to the distal end of the inner tubular member 20.

The endoscopist advances the biopsy forceps 10 through a working channel of the endoscope to the general area of interest, i.e., such as a tissue site. Once in place in the general area of interest, the forceps jaws can be opened by advancing the handle 42 toward the distal end 16 of the forceps 10, thereby advancing the translating member 46 away from the handle 42. This causes the inner tubular member 20 to move away from the handle 42, which in turn causes the actuator housing 60 to be axially moved towards the distal end 16 of the forceps. As the actuator housing 60 moves, the cam pins 68 on the actuator housing 60 move within the cam slots 140 of the cutting jaws 120, causing the cutting jaws 120 to open.

When a biopsy area is identified by the optical fiber 900 using spectrophotometric analysis and/or selected by other methods, the area can now be treated through the lumen using various medical instruments, flushed with saline, or treated with medicine. If other medical instruments are necessary, the optical fiber 900 is removed from the lumen 28, and a new instrument is inserted therein. If a biopsy of the area is necessary, the handle 42 is retracted toward the proximal end 15 of the forceps 10, retracting the inner tubular member 20, and causing the cutting jaws 120 to close and cut a biopsy sample at the exact place that had been treated and/or identified. To take the tissue sample, the endoscopist holding the instrument by the handle portion 12, gently pulls back on the handle 42, retracting the inner tubular member 20, and closing the cutting jaws 120 on the biopsy sample. When the jaws 120 are closed, the endoscopist pulls the entire assembly away from the tissue surface and out of the body. To retrieve the specimen sample from the cutting jaws 120, an instrument is inserted into the hole 128 in the hemispherical cup 126 of one of the cutting jaws 120 or the cutting jaws 120 can be flushed with saline to remove the sample.

Figure 7:
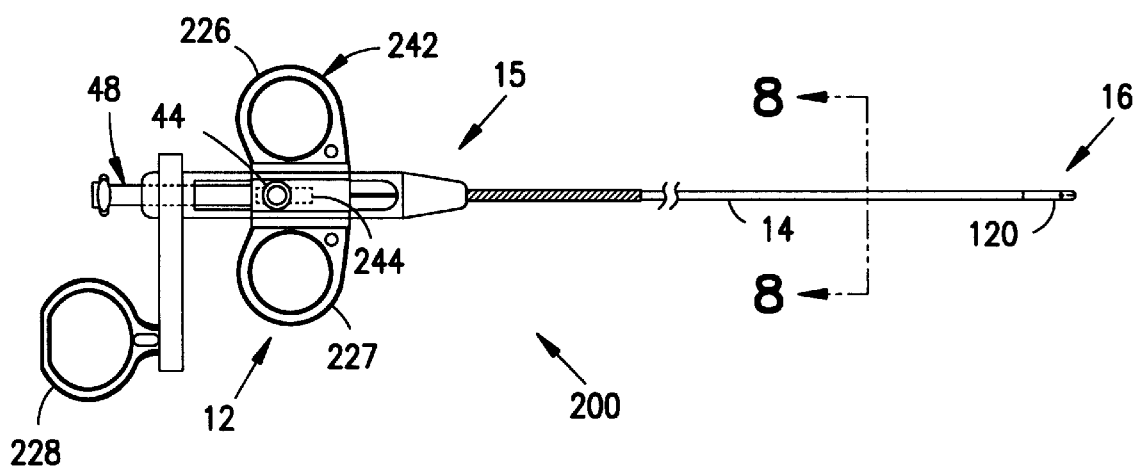
FIG. 7 is a first side elevational view illustrating biopsy forceps constructed in accordance with another embodiment of the present invention.

Referring to FIG. 7, another embodiment of a biopsy forceps of the present invention is generally indicated by reference number 200. The biopsy forceps 200 is generally similar to the biopsy forceps 10 shown in FIG. 1, and accordingly, corresponding elements have been given the same reference number. The biopsy forceps is adapted for use internally of the body, for example in connection with endoscopic, laparoscopic or vascular procedures. The forceps 200 includes a handle portion 12 at the proximal end 15, a middle portion 14 which extends over the main length of the device, and a distal end 16. The distal end 16 includes forceps cutting jaws 120.

Figure 8:
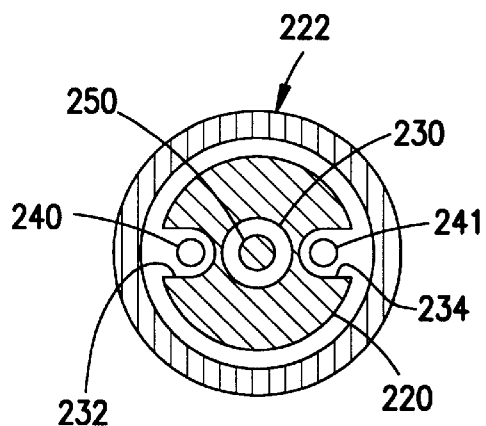
FIG. 8 is a cross-sectional view taken along 8—8 of FIG. 7 illustrating biopsy forceps constructed in accordance with one embodiment of the present invention.

The forceps 200 has a coaxial inner member 220 and an outer tubular member 222, as shown in FIG. 8. The outer tubular member 222 and the inner member 220 each extend generally from the proximal end 15 to the distal end 16 of the forceps 200. The outer tubular member 222, in one embodiment, comprises a finely wound spiral coil of stainless steel as is generally known and used in catheters and guidewires. Alternatively, the outer tubular member 222 could be made using a plastic tube, or a plastic/metal composite structure, in place of the stainless steel spiral coil. The outer tubular member 222 has a lumen therethrough which is sized to received the inner member 220 therein.

In one embodiment, the inner member 220 comprises a polymer tube which is extruded with a lumen 230 therein. Alternatively, the inner member 220 comprises a plastic tube or a combination of metal and plastic. The lumen 230 is sized to receive an optical fiber 250 therein. Secured to at least a portion of the optical fiber 250, the inner member 220 forms a cladding for the optical fiber 250. In addition, grooves 232, 234 are formed in the perimeter of the inner member 220. The grooves 232, 234 form a cavity within the inner member 220 and can also take the form of an indentation or a lumen. In another embodiment, the grooves 232, 234 are disposed on opposite sides of the lumen 230.

Positioned within the grooves 232, 234 of the inner member 220 are a pair of control wires 240, 241, which in one embodiment comprise stainless steel cables. These components, together with outer tubular member 222 and inner member 220 extend over the main length of the device, from the distal end 16 to the handle portion 12 (FIG. 7).

Figure 9:
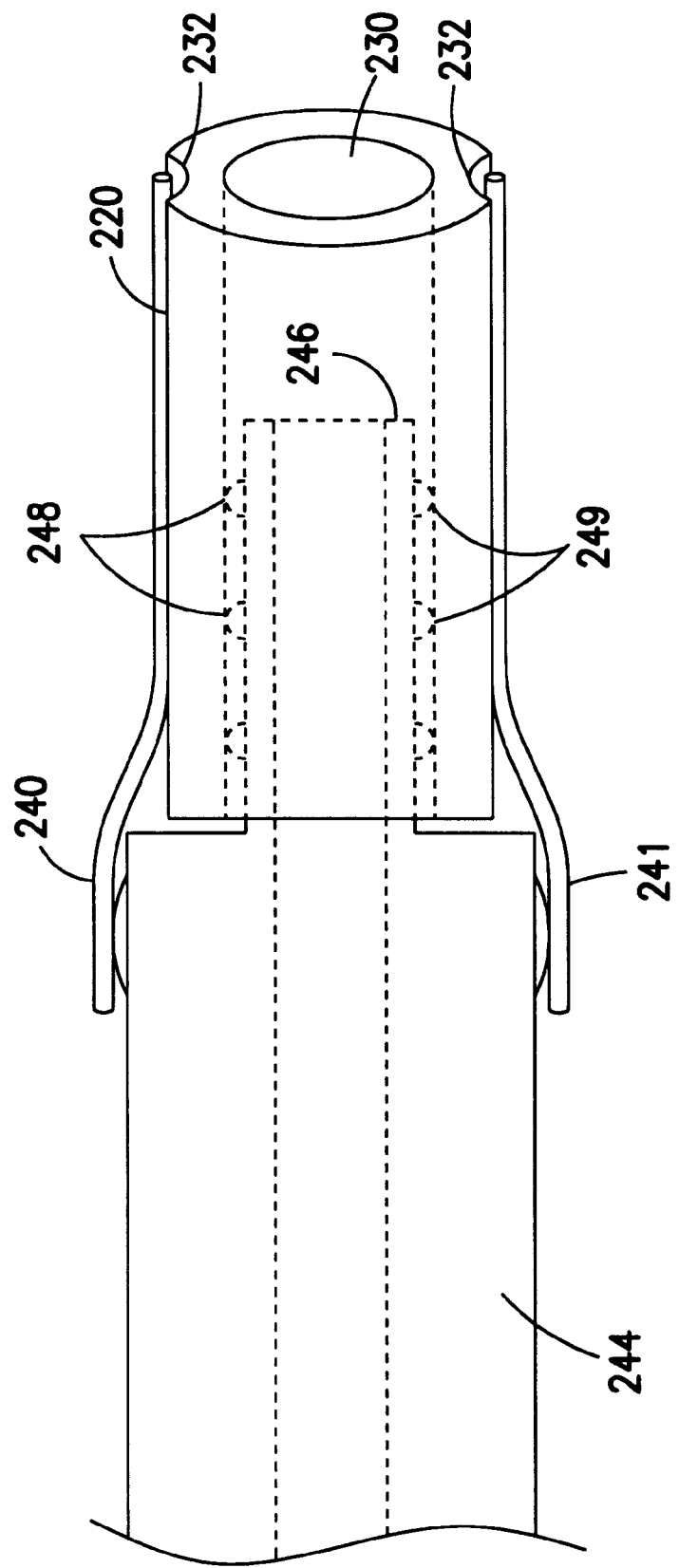
FIG. 9 is a first side elevational view illustrating a translating member assembly for use with biopsy forceps constructed in accordance with one embodiment of the present invention.

The handle portion 12 includes a translating member 244, which in one embodiment, comprises an aluminum block. The handle 242 is fastened to the translation member 244 with fastener 44. Both the inner member 220 and the control wires 240, 241 are secured to the translating member 244, shown in more detail in FIG. 9. The translating member 46 has a projection 246 for securing the inner member 220 with the handle 242. The projection 246, comprising a generally elongate cylinder, has ridges 248, 249 disposed around the perimeter of the projection 246. The ridges 248, 249 of the projection 246 engage the lumen 230 of the inner member 220 and prevent the inner member 220 from disengaging from the handle 242. The control wires 240, 241 are secured to the translating member 244 by either welding, soldering, brazing, adhesives, a mechanical fastener, or other alternatives as known by those skilled in the art.

The inner member 220 and the control wires 240, 241 are secured to translating member 244 which together, in one embodiment, form an actuator mechanism for the forceps 200. Movement of translating member 244 causes axial movement of the inner member 220 and the control wires 240, 241 relative to outer tubular member 222, which is used to actuate the cutting jaws 120. Loops 226, 227, and 228 are provided in handle portion 12 to form finger holes useful in grasping and manipulating the forceps 200 (FIG. 7).

Figure 10:
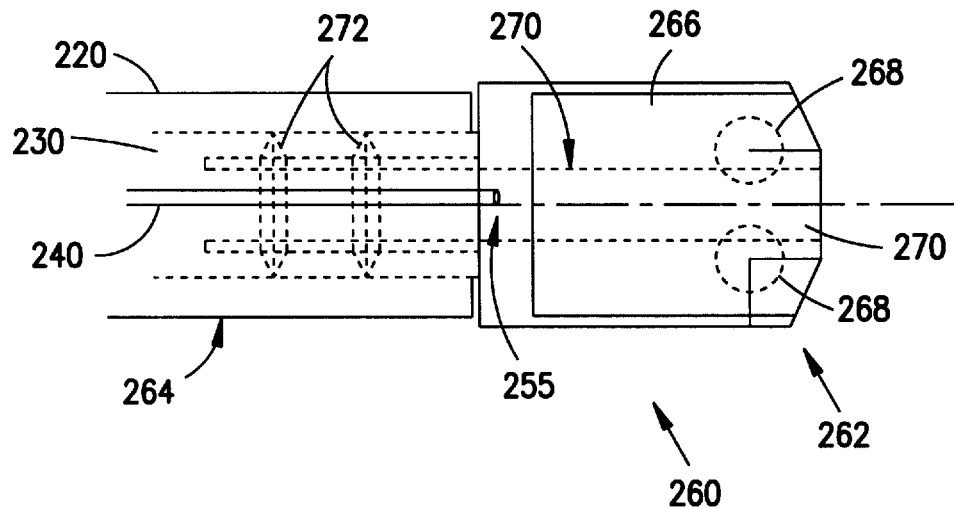
FIG. 10 is a first side elevational view illustrating an actuator housing for use with biopsy forceps constructed in accordance with one embodiment of the present invention.

The inner member 220 extends from the handle portion 12 to the distal end 16. Coupled to the inner member 220 and the control wires 240, 241 at the distal end 16 is an actuator housing 260. The actuator housing 260, shown in more detail in FIG. 10 is, in one embodiment, fabricated from stainless steel material, and generally comprises an elongate cylinder. The actuator housing 260 extends from a first end 262 to a second end 264, and has flats 266 formed proximate the first end 262. Disposed on the flats 266 are cam pins 268 having a generally circular cross-section, as shown. In one embodiment, the cam pins 268 are integral with the flats 266 of the actuator housing 260. To form the cam pins 268 integrally with the flats 266, the actuator housing 260 can be machined or molded from a single piece of material. Alternatively, the cam pins 268 can be integrally formed with the flats 266 by attaching the cam pins 268 to the flats 266 using, for example, adhesive or welding processes. The cam pins 268 are for coupling with the jaws 120, as will be further explained below.

The actuator housing 260 has a bore 270 which extends through the actuator housing 260 from the first end 262 to the second end 264 and is sized to receive the optical fiber 250 therethrough. The bore 270 of the actuator housing 260 aligns with the lumen 230 of the inner member 220 so that access to the distal end 16 is not prevented. The bore 270 allows for the optical fiber 250 to be inserted through the inner tubular member 220 and through the actuator housing 260 to the cutting jaws 120.

The actuator housing 260 has attachment features so that the inner member 220 can be coupled with the actuator housing 260. In one embodiment, the actuator housing 260 has ridges 272 disposed about the perimeter of the actuator housing 260, proximate to the second end 264. The ridges 272 engage the surface of the lumen 230 to retain the inner member 220 on the actuator housing 260. Alternatively, the actuator housing 260 can be coupled with the inner member 220 in other manners, for example, adhesives. The control wires 240, 241 are also secured to the actuator housing 260. In one embodiment, the control wires 240, 241 are secured to the actuator housing at reference number 255 by either welding, soldering, brazing, adhesives, or a mechanical fastener. During use, both the actuator housing 260 and the control wires 240, 241 provide the axial force to the actuation portion 132 of the cutting jaws 120.

The biopsy forceps 200 has a distal housing having the same structure as discussed above, and as shown in FIG. 6. The outer tubular member 222 of the biopsy forceps 200 is secured to the housing, as in the previous embodiment, and therefore will not be further discussed. The biopsy forceps 200 also includes cutting jaws 120.

The cutting jaws 120 are also the same as in the previous embodiment, and one of the cutting jaws 120 is as shown in FIGS. 5a and 5b. Referring to the actuation portion 132, the jaw 122 has a cut out 138 and a cam slot 140. The cut out 138 forms a stationary pivot point for the jaw 122, and receives the pivot pins 100 of the housing 90 therein. The cam slot 140 couples with the cam pins 268 of the actuator housing 260, and allows for radial movement of the jaw 122 about the pivot point as the cam pins 268 of the actuator housing 260 are moved along the axis of the biopsy forceps 200. A further benefit is obtained since the cutting jaws 120 do not move axially during the cutting process. Instead, the cutting jaws 120 rotate about the stationary pivot point. This allows for more precise cutting of the biopsy site identified by the optical fiber.

During operation, referring to FIG. 7, the handle 242 is retracted toward the back of handle portion 12 to close the jaws. This causes movement of the inner member 20, the control wires 240, 241, and the actuator housing 260 toward the handle portion 12, and closes the cutting jaws 120. In this configuration, the distal end 16 of the forceps 10 is of the same narrow diameter as the main body of a forceps catheter, and the closed jaws have a smooth, rounded shape to facilitate introduction and navigation in the vascular, endoscopic or laparoscopic systems. In addition, the cutting jaws are coaxially positioned with respect to the distal end of the inner tubular member.

Once in place in the general area of interest, the cutting jaws 120 can be opened by pushing handle 42 of the control handle forward, away from the handle portion 12. This causes movement of the translation member 244, the inner member 220, the control wires 240, 241, and the actuator housing 260 away from the handle portion 12. The control wires 240, 241 and the inner member 220 push against the actuator housing 260. As the actuator housing 260 moves away from the handle portion 12, the cam pins 268 on the actuator housing 260 move within the cam slots 140 of the cutting jaws 120, and cause the jaws 120 to open. The distal end 16 of the forceps 10 is positioned at the area of contact. The optical fiber 250, when connected to the electro-optic diagnostic apparatus, can then be used for optical biopsy to perform histopathological analysis of the tissue site. When an area of disease is identified and a biopsy of the area is needed, the handle 242 is pulled toward the proximal end 15 of the forceps 10, causing the jaws 120 to close and cut a biopsy sample. The biopsy sample is cut from the exact tissue site identified as the biopsy site without requiring moving or repositioning of the catheter body. The forceps may then be withdrawn from the patient to recover the sample for analysis. The analysis of the withdrawn sample can be conducted using known laboratory techniques to confirm the identification of the tissue sample.

Figure 11:
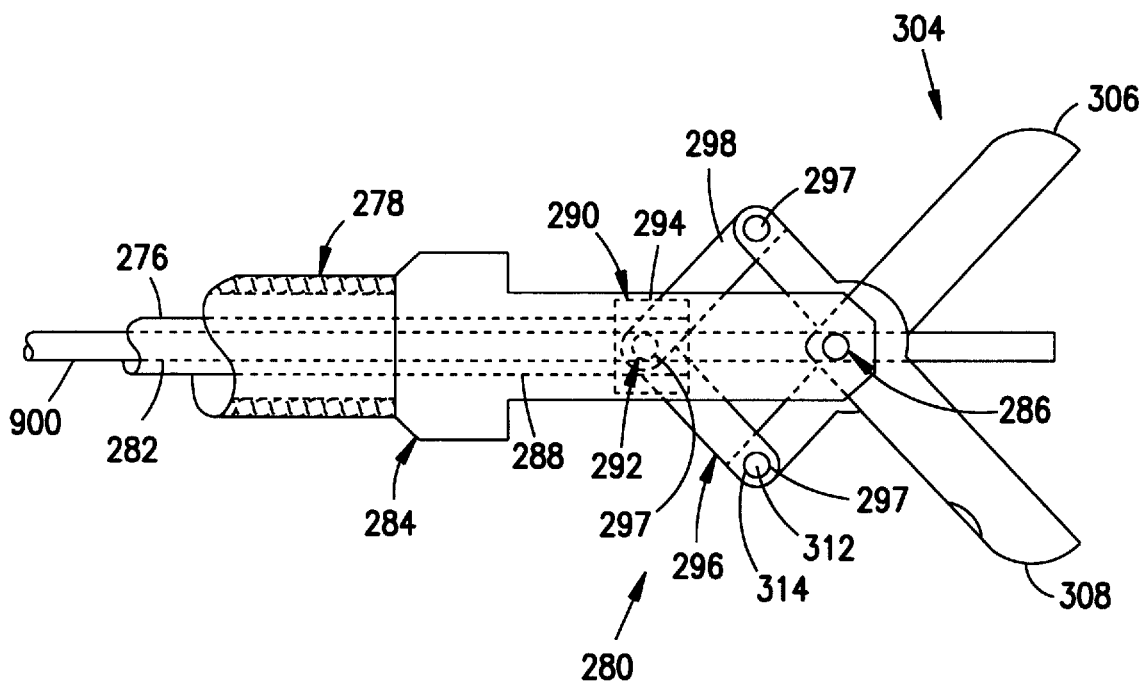
FIG. 11 is a first side elevational view illustrating biopsy forceps constructed in accordance with one embodiment of the present invention.

FIG. 11 illustrates another embodiment of an optical biopsy forceps 280. The optical biopsy forceps 280 includes cutting jaws 304, a coaxial inner member 276 and an outer tubular member 278 which each extend proximate the distal end of the forceps 280. In one embodiment, the inner member 276 is extruded with a lumen 282 therein. Alternatively, the inner member 276 comprises a plastic tube or a combination of metal and plastic. The lumen 282 is sized to receive an optical fiber 900 therein.

The inner tubular member 276 is positioned within the outer tubular member 278 and these components are dimensioned with respect to each other so that inner tubular member 276 moves freely within the outer tubular member 278 to actuate the jaws 304. The optical fiber 900, in one embodiment, is removably disposed within the lumen 282. The inner tubular member 276 is coupled with an actuator housing 290 such that movement of the inner tubular member 276 causes movement of the actuator housing 290.

The actuator housing 290 is, in one embodiment, fabricated from stainless steel material. Alternatively, the actuator housing 290 can be formed from other substantially rigid materials. The actuator housing 290 includes at least one pin 292. The pins 292 are adapted to couple with a link coupling 297 of a first and second link 296, 298.

The actuator housing 290 has a bore 294 therethrough, which allows passage of the optical fiber 900 therethrough. The bore 294 of the actuator housing 290 is aligned with the lumen 282 of the inner tubular member 276, thereby facilitating insertion of the optical fiber 900, or other medical device through the access lumen 282 and through the bore 294. The inner tubular member 276 is coupled with the actuator housing 290, where in one embodiment, the inner tubular member 276 is secured to the actuator housing 290 with a weld. Alternatively, the inner tubular member 276 can be joined with the actuator housing 290 by solder, brazing, or adhesive techniques.

The cutting jaws 304 are comprised of a first jaw 306 and a second jaw 308. The cutting jaws 304 each have a cut out 310 for forming a pivot point for each jaw 304. The cut out 310 is generally circular in shape and sized to receive a projection of a distal housing 284, as will be further discussed below. The cutting jaws 304 each have a coupling 312 for attaching the jaws 304 with a link coupling 297 the first and second links 296, 298. In one embodiment, the coupling 312 comprises a lug 314 disposed on the jaws 304, which couples with the link coupling 297 of the first and second links 296, 298.

The forceps 280 also includes a distal housing 284. The distal housing 284 includes at least one pivot pin 286 disposed thereon. Each pivot pin 286 is adapted to couple with the cut out 310 in each of the cutting jaws 304, and allows the cutting jaws 304 to rotate about the pivot pin 286. The distal housing 284 has a lumen 288 therein which allows passage of the optical fiber 900 therethrough.

In an alternative embodiment, control wires (See FIGS. 7–9) could be coupled with the first and second links 296, 298. For this configuration, the control wires would apply an axial force to the first and second links 296, 298, and would be used to rotate the cutting jaws 304 about the pivot pins 286. In addition, the inner tubular member 276 would be directly coupled with the distal housing 284.

During operation, the handle 42 (FIGS. 1 and 2) is retracted to close the jaws 304. Retraction of the handle 42 causes axial movement of the inner tubular member 276 and the actuator housing 290 toward the handle 42, and closes the cutting jaws 304. After the endoscopist advances the biopsy forceps 280 through a working channel of the endoscope to the general area of interest, the jaws 304 can be opened by advancing the handle 42 toward the distal end of the forceps 280. Advancing the handle 42 causes the inner tubular member 276 to move away from the handle 42, which in turn causes the actuator housing 290 to be axially moved towards the distal end of the forceps. As the actuator housing 290 moves, the first and second links 296, 298 push upon the jaws 304 causing the first and second links 296, 298 to rotate around the couplings on both the actuator housing 290 and the jaws 304. As the links rotate, the cutting jaws 304 rotate about the pivot pins 286 on the distal housing 284 and move to an open position.

The above described embodiment provides many advantages over conventional forceps. For instance, the inner member 220 and the control wires 240, 241 (FIG. 7) both actuate the radial movement of the cutting jaws 120. The combination of devices allows the operator to apply more axial force to the inner member 220 and the control wires 240, 241 thereby resulting in additional torque to the cutting jaws 120. The additional torque provides better cutting actuation, particularly in biopsy sites with tissue that is difficult to cut with the relatively small cutting jaws 120. Another advantage of this embodiment is that the biopsy forceps is disposable, although the biopsy forceps can be reusable. Forming the inner member 220 from the polymer material helps to provide an inexpensive forceps 10 for disposal after use. In addition, using disposable biopsy forceps eliminates the chance of contamination between patients where a biopsy forceps is disposed after use on one patient, which is ideal for patients with highly contagious and dangerous diseases or patients highly susceptible to infection.

Figure 12A:
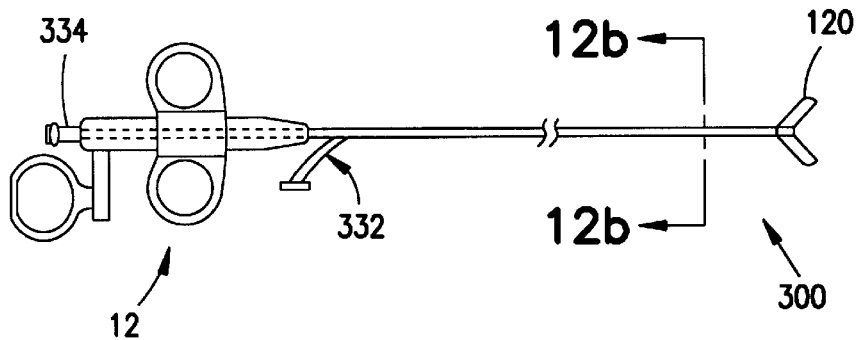
FIG. 12a is a first side elevational view illustrating biopsy forceps constructed in accordance with one embodiment of the present invention.
Figure 12B:
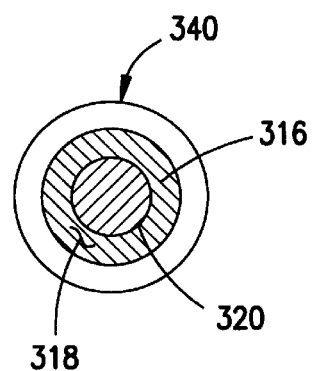
FIG. 12b is a cross-sectional view taken along 12b—12b of FIG. 12a illustrating biopsy forceps constructed in accordance with one embodiment of the present invention.

FIGS. 12a and 12b illustrate yet another embodiment of the present invention. A biopsy forceps 300 is provided having multiple access lumens. The general configuration of the biopsy forceps 300 is the same as the first discussed embodiment where an inner tubular member 320 is slidably received by an outer tubular member 340. The inner tubular member 320 actuates the cutting jaws 120, as discussed above. In one embodiment, the inner tubular member 320 has a plurality of lumens disposed therein. In at least one of the lumens, an optical fiber is disposed therethrough. The plurality of lumens allow for other components or materials (such as fluids) to be inserted through the inner tubular member simultaneously with the optical fiber. Alternatively, in another embodiment, a gap 316 between the inner surface of the outer tubular member and the outer surface of the inner tubular member 320 provides a secondary lumen 318. The secondary lumen 318 allows for fluids such as saline or medicine to be administered to the biopsy area. During use, the fluids travel through the secondary lumen 318 and are expelled through openings between the distal housing 90 and the cutting jaws 120 (FIG. 3) to treat the biopsy area. Access to the primary lumen is at a primary port 334. To access the secondary lumen 318 or the multiple lumens described above, a secondary port 332 is provided proximate the handle portion 12. The secondary port, in one embodiment, comprises a luer fitting as known by those skilled in the art.

Figure 13:
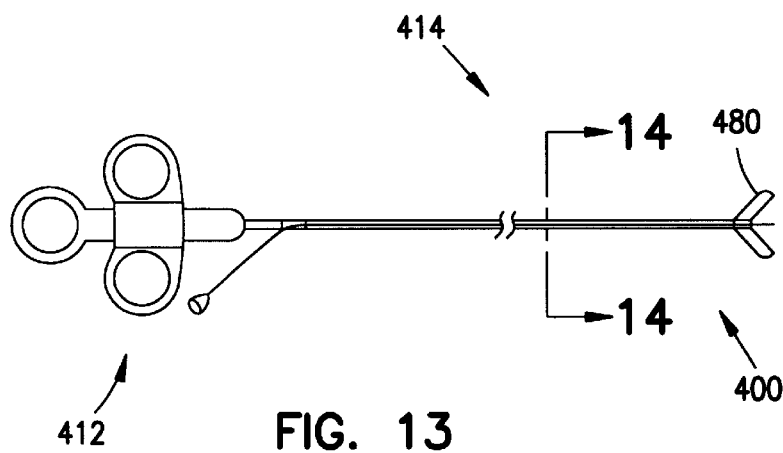
FIG. 13 is a first side elevational view illustrating biopsy forceps constructed in accordance with one embodiment of the present invention.
Figure 14:
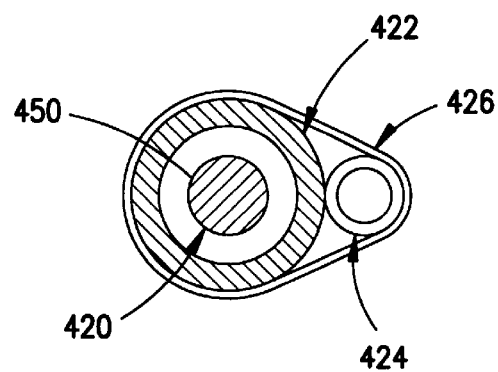
FIG. 14 is a cross-sectional view taken along 14—14 of FIG. 13 illustrating biopsy forceps constructed in accordance with one embodiment of the present invention.

FIGS. 13 and 14 illustrate another embodiment of the present invention. In this configuration, a biopsy forceps 400 are provided with cutting jaws 480, a handle portion 412, and a main body 414 in between. The main body 414 has an inner tubular member 420, which actuates the cutting jaws 480 and is disposed within an outer tubular member 422, as discussed above. Disposed within the inner tubular member 420 is an optical fiber 450. A third tubular member 424 is coupled with the main body 420. In one embodiment, the third tubular member 424 is secured to the outer surface of the outer tubular member 422 as shown in FIG. 14 by welding, brazing, soldering, or adhesive. In another embodiment, a polymer heat-shrink jacket 426 is placed over the outer tubular member 422 and the third tubular member 424 to thereby couple the third tubular member 424 with the outer tubular member 422. The outer jacket coating provides the forceps 400 with a smooth surface for ease of use within the patient.

Figure 15A:
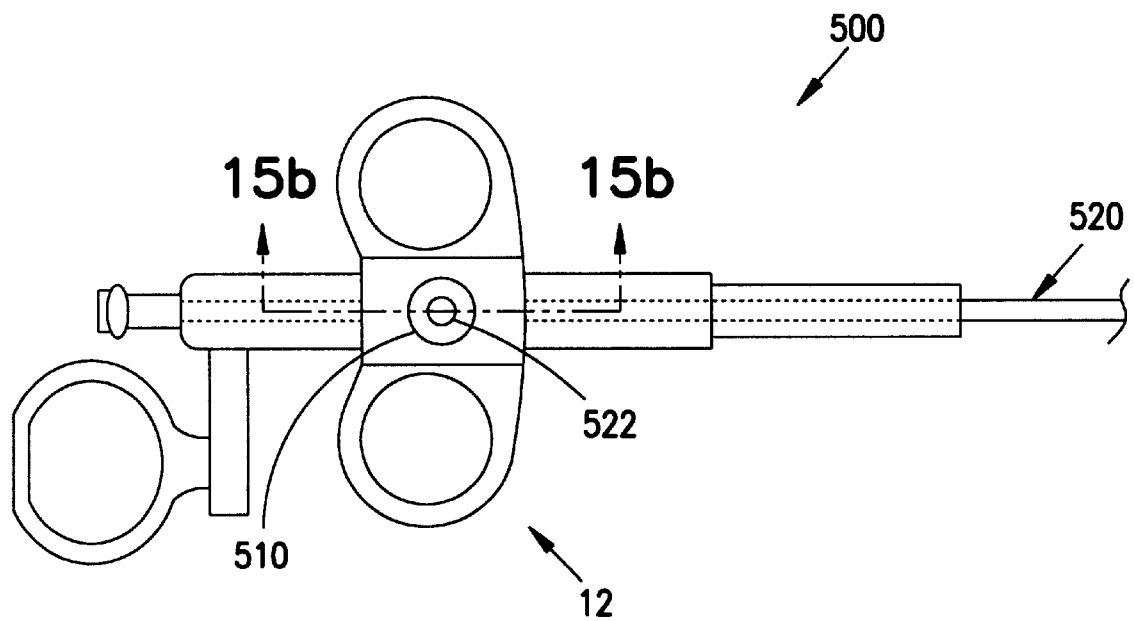
FIG. 15a is a first side elevational view illustrating biopsy forceps constructed in accordance with one embodiment of the present invention.
Figure 15B:
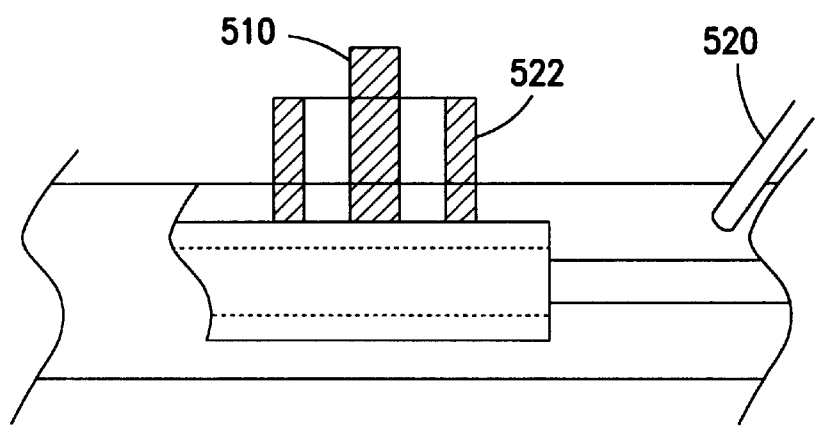
FIG. 15b is a cross-sectional view taken along 15b—15b of FIG. 15a illustrating biopsy forceps constructed in accordance with one embodiment of the present invention.

In another embodiment of the invention, the above biopsy forceps 500 are provided with electro-cauterizing capability. In this configuration shown in FIGS. 15a and 15b, using the biopsy forceps 500 as described above, a connector pin 510 is provided on the handle portion 12. The connector pin 510 forms an electrical connection which is compatible with standard electro/surgical equipment. In one embodiment, a protective collar 522 surrounds the connector pin 510, preventing inadvertent contact with the connector pin 510. The collar 522 protects the connector pin 510 from being damaged. The inner tubular member 520 comprises a stainless steel tube, which is coupled with the connector pin 510. Alternatively, the inner tubular member 520 comprises a polymer tube with steel control wires, as described above. During use, a radio frequency current is coupled with the connector pin 510. The connector pin 510 allows a current path to the stainless steel tube, or the stainless steel pull wire, depending on the embodiment. The current path would follow the stainless steel tube or wires to the cutting jaws disposed at the distal end of the biopsy forceps. The jacket 426 acts as an insulator over the length of the forceps 500, with the metallic jaws acting as the cauterizing device. The connector pin 510, as known by those skilled in the art, is coupled with equipment having the electro-surgical standard for radio frequency current. The radio frequency current allows for cauterizing capability of the biopsy forceps 500 in the biopsy site using either mono or bipolar modes.

Figure 16A:
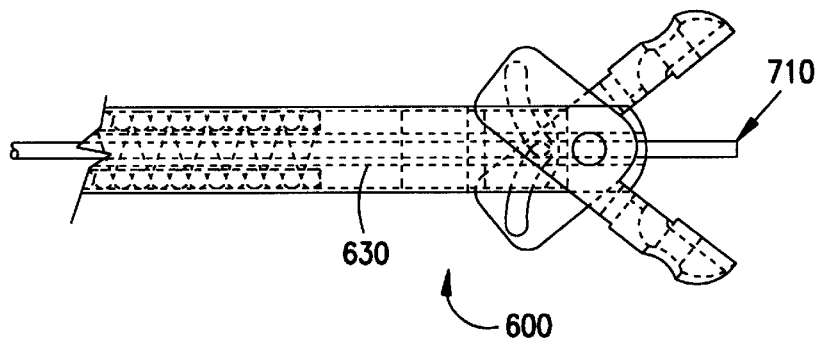
FIG. 16a is a first side elevational view illustrating a biopsy forceps having an ultrasonic probe disposed therethrough in accordance with one embodiment of the present invention.
Figure 16B:
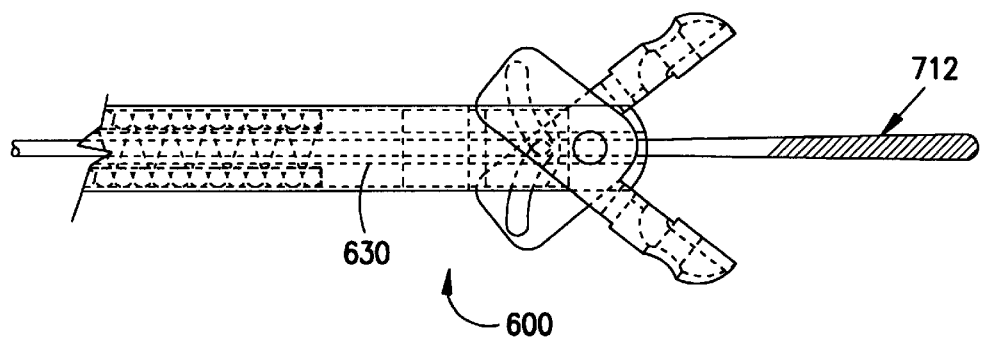
FIG. 16b is a first side elevational view illustrating a biopsy forceps having a guidewire disposed therethrough in accordance with one embodiment of the present invention.
Figure 16C:
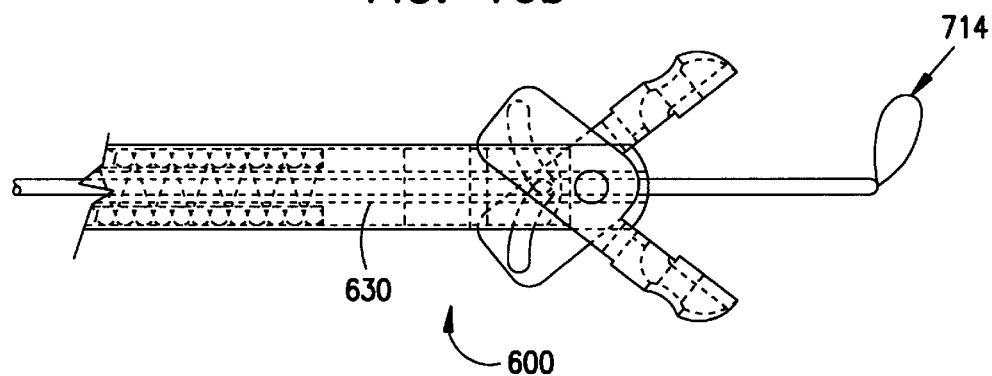
FIG. 16c is a first side elevational view illustrating a biopsy forceps having a snare disposed therethrough in accordance with one embodiment of the present invention.
Figure 16D:
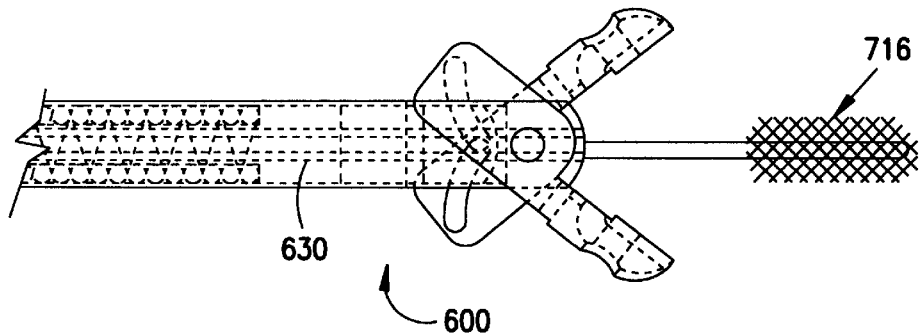
FIG. 16d is a first side elevational view illustrating a biopsy forceps having a cytology brush disposed therethrough in accordance with one embodiment of the present invention.
Figure 16E:
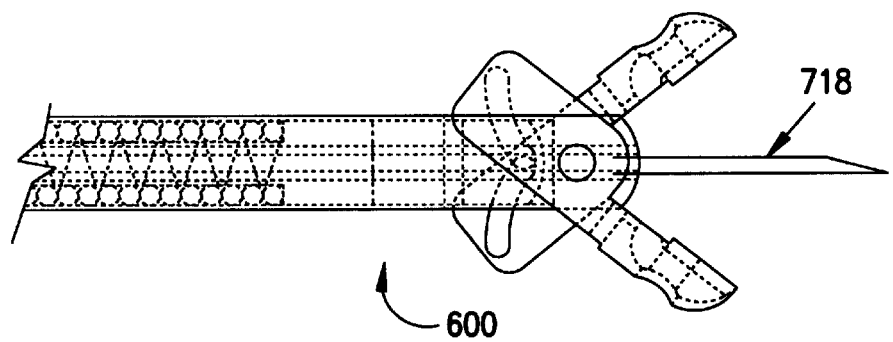
FIG. 16e is a first side elevational view illustrating a biopsy forceps having a needle disposed therethrough in accordance with one embodiment of the present invention.
Figure 16F:
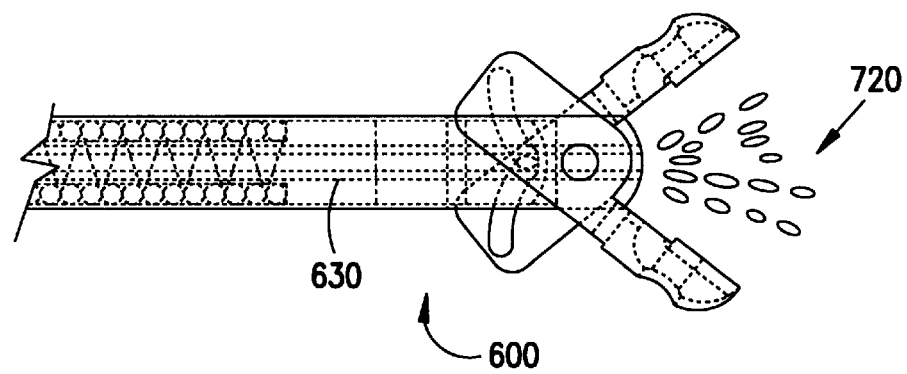
FIG. 16f is a first side elevational view illustrating a biopsy forceps having saline flushed therethrough in accordance with one embodiment of the present invention.
Figure 16G:
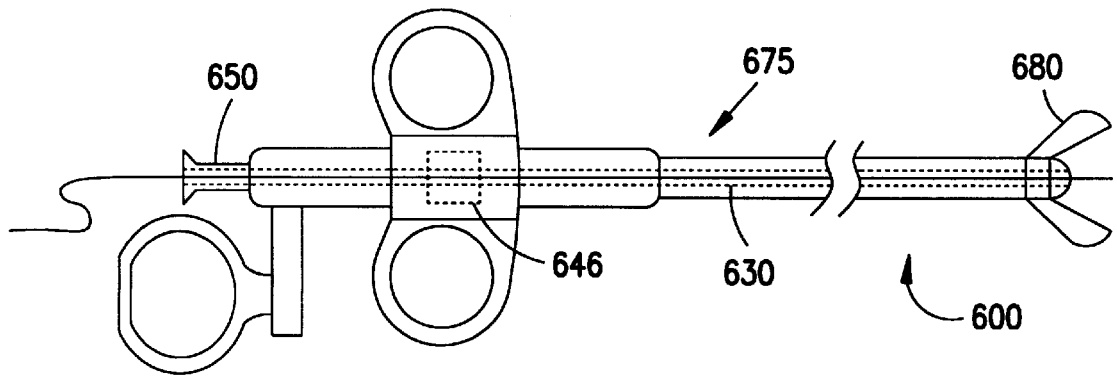
FIG. 16g is a first side elevational view illustrating a biopsy forceps having an instrument inserted therethrough in accordance with one embodiment of the present invention.

The lumen of the above biopsy forceps allows for a number of medical instruments to be inserted through the biopsy forceps once the optical fiber is removed, and the instruments are also axially aligned with the cutting jaws. Another embodiment of the present invention includes medical devices slidably engaged within the access lumen 630 of biopsy forceps 600. As shown in FIGS. 16a–16e, many instruments can be inserted into the lumen 630 of the inner tubular member 620, including, but not limited to: ultra sonic probe 710, guidewires 712, a snare 714, a cytology brush 716, and a needle 718. In addition, the area to be sampled by the biopsy forceps 600 can be flushed with saline 720, medicine, or other fluids as shown in FIG. 16f. Alternatively, suction can be applied to the lumen 630 for removing excess loose material or fluid from the biopsy site. As shown in FIG. 16g, each instrument is inserted into an access port 650 and extends through a translating member 646, through a middle portion 675, and through cutting jaws 680 of the forceps 600. The instruments are used for treating the tissue in the area adjacent the distal end of the forceps 600, which is aligned with the axis of the lumen 630.

The present invention has provided a biopsy forceps having an access lumen and an optical fiber. An important feature of the invention is that the lumen of the inner tubular member is coaxial with the zone where the two jaws intersect and the sample is taken. Thus, there is no offset error between the spot where the various medical instruments or treatments are used and the spot from which the biopsy sample will be taken. In addition, the physician has more options in treating the area where the biopsy sample is taken. For instance, the area can first be flushed with saline, or treated with medicine. The biopsy forceps provides a further advantage in that an area can be treated with saline and/or with medicine without having to remove the biopsy forceps from the body. Alternatively, one of many instruments can be used to treat the biopsy area prior to the biopsy. These features, together with the slim and compact profile of the device when the jaws are retracted, are a great improvement over prior art devices. One of the advantages of forceps 10 as compared to forceps 200 is, because the control wires 240, 241 are not required, a larger diameter lumen can be used to accommodate larger sized instruments.

A further advantage of the present invention is that since the optical fiber 900 is removable from the biopsy forceps 10, the biopsy forceps 10 is reusable. When the optical fiber 900 needs to be replaced, the entire biopsy forceps 10 does not need to be discarded. Instead, a new optical fiber 900 is inserted through the central access lumen 28 when the use of the previous optical fiber 900 is exhausted. Removing the optical fiber 900 from the biopsy forceps 10 also allows for the forceps 10 to be cleaned and sterilized more extensively using more strenuous processes. In some sterilization techniques, the optical fiber 900 degrades during the cleaning process. Thus, removing the fiber 900 during the more strenuous cleaning processes prolongs the useful life of the optical fiber 900.

It will be appreciated from the foregoing that we have provided an improved biopsy forceps and system which provides the physician a greater degree of accuracy and control over the biopsy treatment and sampling process than was previously possible. While we have illustrated the invention with the illustrated embodiments of the invention, it will be appreciated that variations of shapes, materials and assembly are possible, within the scope of the invention.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A biopsy forceps for sampling tissue from an area of interest, the biopsy forceps comprising:
   a flexible outer tubular member having a first lumen therethrough, the outer tubular member extending from a proximal end to a distal end and adapted for insertion into a working channel of an endoscope;
   cutting jaws mounted proximate to the distal end of the outer tubular member for selective opening and closing in a biopsy cutting movement, the cutting jaws mounted with a closed cutting position co-axially aligned with the first lumen;
   an inner tubular member having a second lumen therethrough, the inner tubular member extending through the first lumen of the outer tubular member and operatively connected to open and close the cutting jaws;
   a removable optical fiber removably disposed within the second lumen of the inner tubular member, the optical fiber extending from a proximal end to a distal end and said proximal end of the optical fiber adapted for connection to a spectrophotometric tissue analysis system, said optical fiber removable during use of the biopsy forceps;
   an actuator mechanism coupled with the proximal end of the outer tubular member and the inner tubular member, where the actuator mechanism is operatively coupled with the inner tubular member; and
   an access port communicatively coupled with the second lumen.

2. The biopsy forceps as recited in claim 1, wherein movement of the inner tubular member causes radial movement of the cutting jaws about fixed pivot pins, said cutting jaws pivotally mounted to pivot about a common pivotal axis.

3. The biopsy forceps as recited in claim 1, wherein the outer tubular member comprises a coiled stainless steel tube.

4. The biopsy forceps as recited in claim 1, wherein the inner tubular member comprises a coiled stainless steel tube.

5. The biopsy forceps as recited in claim 1, wherein the actuator mechanism is coupled with the inner tubular member such that actuating the actuator mechanism causes axial translation of the inner tubular member thereby causing closing and opening movement of the cutting jaws aligned with the axis of the inner tubular member.

6. The biopsy forceps as recited in claim 1, wherein the biopsy forceps further comprises an actuator housing having a bore coaxially aligned with the second lumen, and the actuator housing is coupled with the distal end of the inner tubular member for actuating the cutting jaws.

7. The biopsy forceps as recited in claim 1, wherein the second lumen of the inner tubular member has a first diameter and an outer diameter of the optical fiber has a second diameter, and the first diameter is greater than the second diameter and adapted for fluid to be flushed therethrough.

8. The biopsy forceps as recited in claim 1, the biopsy forceps further comprising an electrical connection in the proximal end electrically connected for cauterizing tissue proximate the distal end of the forceps via electrosurgical current.

9. A biopsy forceps for sampling tissue from an area of interest, the biopsy forceps comprising:
   a flexible outer tubular member having a first lumen therethrough, the outer tubular member extending from a proximal end to a distal end and adapted for insertion into a working channel of an endoscope;
   cutting jaws mounted proximate to the distal end of the outer tubular member for selective opening and closing in a biopsy cutting movement, the cutting jaws mounted with a closed cutting position co-axially aligned with the first lumen; and
   an inner tubular member having a second lumen therethrough, the inner tubular member extending through the first lumen of the outer tubular member and operative to open and close the cutting jaws;
   a removable optical fiber removably disposed within the second lumen of the inner tubular member, the optical fiber extending from a proximal end to a distal end and said proximal end of the optical fiber adapted for connection to an electro-optical histopathological system, said optical fiber removable during use of the biopsy forceps;
   a handle portion coupled with the proximal end of the outer tubular member and the inner tubular member, the handle portion comprising:
   a handle;
   a translating member operatively coupled with the handle and the inner tubular member, where moving the handle causes axial movement to the inner tubular member to open and close the cutting jaws; and
   an access port communicatively coupled with the second lumen.

10. The biopsy forceps as recited in claim 9, wherein the forceps further comprises an actuator housing operatively coupled with the inner tubular member and the cutting jaws, and a distal housing coupled with the cutting jaws and the outer tubular member.

11. The biopsy forceps as recited in claim 10, wherein the actuator housing has at least two cam pins integral therewith, the cutting jaws each have a cam slot, the distal housing has pivot pins integral therewith, and the actuator housing cam pins are received by the cam slots of the cutting jaws wherein movement of the cam pins causes radial movement of the cutting jaws about the pivot pins, said cutting jaws pivotally mounted to pivot about a common pivotal axis.

12. The biopsy forceps as recited in claim 10, wherein the actuator housing comprises at least a first link and a second link rotatably coupled with the cutting jaws and the actuator housing, and the distal housing having at least one pivot pin integral therewith, where the cutting jaws are adapted to rotate about the pivot pins, said cutting jaws pivotally mounted to pivot about a common pivotal axis.

13. The biopsy forceps as recited in claim 9, wherein the biopsy forceps further comprises at least one luer fitting communicatively coupled with the second lumen of the inner tubular member.

14. The biopsy forceps as recited in claim 9, wherein each cutting jaw has a cup portion for receiving the biopsy sample therein, and at least one cup has an aperture therein, wherein said aperture facilitates the removal of biopsy samples from the cup of the cutting jaws.

15. The biopsy forceps as recited in claim 9, wherein the inner tubular member has at least two lumens therein, and the optical fiber is disposed in one of the lumens.

16. A biopsy forceps for sampling tissue from an area of interest, the biopsy forceps comprising:
    a flexible outer tubular member having a first lumen therethrough, the outer tubular member extending from a proximal end to a distal end and adapted for insertion into a working channel of an endoscope;
    cutting jaws mounted proximate to the distal end of the outer tubular member for selective opening and closing in a biopsy cutting movement and having a closed cutting position aligned with the first lumen, the cutting jaws rotatably mounted on pivot pins, said cutting jaws pivotally mounted to pivot about a common pivotal axis; and
    an inner tubular member having a second lumen therethrough, the inner tubular member extending through the first lumen of the outer tubular member and having at least one groove disposed therein;
    a removable optical fiber disposed within the second lumen of the inner member where the optical fiber is affixed to at least a portion of the inner member, the optical fiber extending from a proximal end to a distal end and said proximal end of the optical fiber adapted for connection to an electro-optical histopathological analysis system, said optical fiber removable during use of the biopsy forceps;
    at least one control wire disposed in at least one of the grooves of the inner member and extending from the proximal end to the distal end, where the control wire and the inner member are operatively coupled with the cutting jaws such that axial movement of the control wire and the inner member causes radial movement of the cutting jaws about stationary pivot pins; and
    an actuator mechanism coupled with the proximal end of the outer tubular member and the inner tubular member, where the actuator mechanism is operatively coupled with the inner tubular member.

17. The biopsy forceps as recited in claim 16, wherein the inner member has two grooves each disposed in an outer surface of the inner member, and each groove having the control wire disposed therein.

18. The biopsy forceps as recited in claim 16, wherein the inner member is comprised of a polymer tube.

19. The biopsy forceps as recited in claim 16, wherein the forceps further comprises an actuator housing operatively coupled with the inner tubular member and the cutting jaws, and a distal housing coupled with the cutting jaws and the outer tubular member.

20. The biopsy forceps as recited in claim 19, wherein the actuator housing has at least two cam pins integral therewith, the cutting jaws each have a cam slot, the distal housing has pivot pins integral therewith, and the actuator housing cam pins are received by the cam slots of the cutting jaws wherein movement of the cam pins causes radial movement of the cutting jaws about the pivot pins about a common pivotal axis.

21. A biopsy forceps for sampling tissue from an area of interest, the biopsy forceps comprising:
    a flexible outer tubular member having a first lumen therethrough, the outer tubular member extending from a proximal end to a distal end and adapted for insertion into a working channel of an endoscope;
    cutting jaws mounted proximate to the distal end of the outer tubular member for selective opening and closing in a biopsy cutting movement, the cutting jaws mounted with a closed cutting position aligned with the first lumen;
    an inner tubular member having a second lumen therethrough wherein the second lumen is adapted to receive devices, the inner tubular member extending through the first lumen of the outer tubular member and operative to open and close the cutting jaws;
    a removable optical fiber removably disposed within the second lumen of the inner tubular member, said optical fiber removable during use of the biopsy forceps;
    an actuator mechanism coupled with the proximal end of the outer tubular member and the inner tubular member, where the actuator mechanism is operatively coupled with the inner tubular member;
    a first access port communicatively coupled with the second lumen;
    a third tubular member coupled with an outer surface of the outer tubular member, the third tubular member extending from the proximal to the distal ends and having a third lumen therein; and
    a second access port coupled with the proximal end of the third tubular member.

22. The biopsy forceps as recited in claim 21, wherein the forceps further comprises shrink tubing disposed over the third tubular member and the outer tubular member.

23. A biopsy forceps for sampling tissue from an area of interest, the biopsy forceps comprising:
    a proximal end and a distal end;
    a flexible outer tubular member having a first lumen therethrough, the outer tubular member extending from a proximal end to a distal end and adapted for insertion into a working channel of an endoscope;
    cutting jaws mounted proximate to the distal end of the outer tubular member for selective opening and closing in a biopsy cutting movement, the cutting jaws mounted with a closed cutting position co-axially aligned with the first lumen;
    an inner tubular member having a second lumen therethrough, the inner tubular member extending through the first lumen of the outer tubular member and operatively connected to open and close the cutting jaws;
    an actuator mechanism coupled with the proximal end of the outer tubular member and the inner tubular member, where the actuator mechanism is operatively coupled with the inner tubular member; and an access port communicatively coupled with the second lumen.

24. The biopsy forceps of claim 23, further comprising a medical instrument removably disposed within the second lumen of the inner tubular member extending from a proximal end to a distal end, the medical instrument adapted for use in the area of interest to treat a biopsy sampling area, the forceps providing accurate alignment with repetitive introduction and withdrawal of medical instruments during use.

25. The biopsy forceps of claim 24, wherein the medical instrument comprises an ultrasonic probe.

26. The biopsy forceps of claim 24, wherein the medical instrument comprises an optical fiber.

27. The biopsy forceps of claim 24, wherein the medical instrument comprises at least one guidewire.

28. The biopsy forceps of claim 24, wherein the medical instrument comprises a snare.

29. The biopsy forceps of claim 24, wherein the medical instrument comprises a cytology brush.

30. The biopsy forceps of claim 24, wherein the medical instrument comprises a needle.

31. The biopsy forceps of claim 23, wherein the second lumen is adapted for flushing the area of interest.

32. The biopsy forceps of claim 23, wherein the second lumen is adapted for suctioning the area of interest.

33. A biopsy forceps for sampling tissue from an area of interest, the biopsy forceps comprising:
a flexible outer tubular member having a first lumen therethrough, the outer tubular member extending from a proximal end to a distal end and adapted for insertion into a working channel of an endoscope;
cutting jaws mounted proximate to the distal end of the outer tubular member for selective opening and closing in a biopsy cutting movement, the cutting jaws mounted with a closed cutting position co-axially aligned with the first lumen; and
an inner tubular member having a second lumen therethrough, the inner tubular member extending through the first lumen of the outer tubular member and operative to open and close the cutting jaws;
a handle portion coupled with the proximal end of the outer tubular member and the inner tubular member, the handle portion comprising:
a handle;
a translating member operatively coupled with the handle and the inner tubular member, where moving the handle causes axial movement to the inner tubular member to open and close the cutting jaws; and
an access port communicatively coupled with the second lumen.

34. The biopsy forceps as recited in claim 33, wherein the forceps further comprises an actuator housing operatively coupled with the inner tubular member and the cutting jaws, and a distal housing coupled with the cutting jaws and the outer tubular member.

35. The biopsy forceps as recited in claim 34, wherein the actuator housing has at least two cam pins integral therewith, the cutting jaws each have a cam slot, the distal housing has pivot pins integral therewith, and the actuator housing cam pins are received by the cam slots of the cutting jaws wherein movement of the cam pins causes radial movement of the cutting jaws about the pivot pins, about a common pivotal axis.

36. The biopsy forceps as recited in claim 34, wherein the actuator housing comprises at least a first link and a second link rotatably coupled with the cutting jaws and the actuator housing, and the distal housing having pivot pins integral therewith, where the cutting jaws are adapted to rotate about the pivot pins, about a common pivotal axis.

37. The biopsy forceps as recited in claim 33, wherein the biopsy forceps further comprises at least one luer fitting communicatively coupled with the second lumen of the inner tubular member.

38. The biopsy forceps as recited in claim 33, wherein each cutting jaw has a cup portion for receiving the biopsy sample therein, and at least one cup has an aperture therein, wherein said aperture facilitates the removal of biopsy samples from the cup of the cutting jaws.

39. The biopsy forceps of claim 33, further comprising a removable optical fiber removably disposed within the second lumen of the inner tubular member, the optical fiber extending from a proximal end to a distal end and said proximal end of the optical fiber adapted for connection to an electro-optical histopathological system, said optical fiber removable during use of the biopsy forceps.

40. The biopsy forceps as recited in claim 39, wherein the inner tubular member has at least two lumens therein, and the optical fiber is disposed in one of the lumens.

41. The biopsy forceps of claim 33, further comprising a medical instrument removably disposed within the second lumen of the inner tubular member and adapted for use in the area of interest to treat a biopsy sampling area, the forceps providing accurate alignment with repetitive introduction and withdrawal of medical instruments during use.

42. The biopsy forceps of claim 41, wherein the medical instrument comprises an ultrasonic probe.

43. The biopsy forceps of claim 41, wherein the medical instrument comprises at least one guidewire.

44. The biopsy forceps of claim 41, wherein the medical instrument comprises a snare.

45. The biopsy forceps of claim 41 wherein the medical instrument comprises a cytology brush.

46. The biopsy forceps of claim 41, wherein the medical instrument comprises a needle.

47. The biopsy forceps of claim 33 wherein the second lumen is adapted for flushing the area of interest.

48. The biopsy forceps of claim 33, wherein the second lumen is adapted for suctioning the area of interest.

49. A biopsy forceps for sampling tissue from an area of interest, the biopsy forceps comprising:
a flexible outer tubular member having a first lumen therethrough, the outer tubular member extending from a proximal end to a distal end and adapted for insertion into a working channel of an endoscope;
cutting jaws mounted proximate to the distal end of the outer tubular member for selective opening and closing in a biopsy cutting movement and having a closed cutting position aligned with the first lumen, the cutting jaws rotatably mounted on pivot pins, said cutting jaws pivotally mounted to pivot about a common pivotal axis; and
an inner tubular member having a second lumen therethrough, the inner tubular member extending through the first lumen of the outer tubular member and having at least one groove disposed therein;
at least one control wire disposed in at least one of the grooves of the inner member and extending from the proximal end to the distal end, where the control wire and the inner member are operatively coupled with the cutting jaws such that axial movement of the control wire and the inner member causes radial movement of the cutting jaws about stationary pivot pins; and
an actuator mechanism coupled with the proximal end of the outer tubular member and the inner tubular member, where the actuator mechanism is operatively coupled with the inner tubular member.

* * * * *

UNITED STATES PATENT AND TRADEMARK OFFICE
CERTIFICATE OF CORRECTION

PATENT NO. : 6,066,102

DATED : May 23, 2000

INVENTOR(S) : Townsend et al.

It is certified that error appears in the above-identified patent and that said Letters Patent is hereby corrected as shown below:

On the Title Page,

Item [56]

In the title delete --AND METHOD OF DIAGNOSING TISSUE--

Signed and Sealed this

Twenty-seventh Day of March, 2001

*Attest:*

NICHOLAS P. GODICI

*Attesting Officer*   Acting Director of the United States Patent and Trademark Office